(12) United States Patent
Lu et al.

(10) Patent No.: US 10,495,594 B2
(45) Date of Patent: Dec. 3, 2019

(54) IMPEDANCE TESTING WITH ALTERNATING CURRENT FREQUENCY CONTROL

(71) Applicant: Hewlett-Packard Development Company, L.P., Houston, TX (US)

(72) Inventors: Sirena C. Lu, San Diego, CA (US); Melinda M. Valencia, Chula Vista, CA (US); Jeremy Sells, Albany, OR (US); Manish Giri, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 339 days.

(21) Appl. No.: 15/112,618

(22) PCT Filed: Jan. 30, 2015

(86) PCT No.: PCT/US2015/013854
§ 371 (c)(1),
(2) Date: Jul. 19, 2016

(87) PCT Pub. No.: WO2015/116975
PCT Pub. Date: Aug. 6, 2015

(65) Prior Publication Data
US 2016/0377567 A1    Dec. 29, 2016

Related U.S. Application Data

(63) Continuation-in-part of application No. PCT/US2014/013748, filed on Jan. 30, 2014.

(51) Int. Cl.
*G01N 17/00* (2006.01)
*G01N 27/06* (2006.01)
(Continued)

(52) U.S. Cl.
CPC ........ *G01N 27/06* (2013.01); *B01L 3/502715* (2013.01); *G01N 15/0266* (2013.01);
(Continued)

(58) Field of Classification Search
CPC combination set(s) only.
See application file for complete search history.

(56) References Cited

U.S. PATENT DOCUMENTS 4,404,636 A * 9/1983 Campbell, Jr. ......... H04M 3/30
324/650
4,420,720 A   12/1983 Newton et al.
(Continued)

FOREIGN PATENT DOCUMENTS

CN   1916639       2/2007
CN   102360025 A   2/2012
(Continued)

OTHER PUBLICATIONS

Tao Sun et al: "Single-cell microfluidic impedance cytometry: a review", Microfluidics and Nanofluidics, Springer, Berlin, DE, vol. 8, No. 4, Mar. 6, 2010 (Mar. 6, 2010), pp. 423-443, XP019785777, ISSN: 1613-4990, *the whole document*.
(Continued)

*Primary Examiner* — Melissa J Koval
*Assistant Examiner* — Courtney G McDonnough
(74) *Attorney, Agent, or Firm* — Perry + Currier Inc

(57) ABSTRACT

A controller outputs control signals controlling a frequency source to selectively apply different nonzero frequencies of alternating current at different times to an electric sensor within a microfluidic channel.

18 Claims, 11 Drawing Sheets

(51) Int. Cl.
*G01N 15/02* (2006.01)
*G01N 15/10* (2006.01)
*G01N 15/14* (2006.01)
*G01N 27/12* (2006.01)
*B01L 3/00* (2006.01)
*G01N 15/12* (2006.01)

(52) U.S. Cl.
CPC ......... *G01N 15/1031* (2013.01); *G01N 15/12* (2013.01); *G01N 15/1484* (2013.01); *G01N 27/12* (2013.01); *B01L 2200/10* (2013.01); *B01L 2300/0645* (2013.01); *G01N 2015/1006* (2013.01); *G01N 2015/1493* (2013.01)

(56) References Cited

U.S. PATENT DOCUMENTS

| | | |
|---|---|---|
| 5,965,410 A | 10/1999 | Chow et al. |
| 6,426,615 B1 | 7/2002 | Mehta |
| 6,437,551 B1 | 8/2002 | Krulevitch et al. |
| 6,967,489 B2 | 11/2005 | Brooks et al. |
| 8,390,304 B2 | 3/2013 | Patterson |
| 8,440,093 B1 | 5/2013 | Nassef et al. |
| 8,642,287 B2 | 2/2014 | Wang et al. |
| 8,795,497 B2 | 8/2014 | Sato et al. |
| 8,841,924 B2 | 9/2014 | Reccius et al. |
| 9,566,581 B2 | 2/2017 | Imran |
| 2002/0081228 A1 | 6/2002 | Hui et al. |
| 2002/0125959 A1 | 9/2002 | Atsumi et al. |
| 2003/0094953 A1 | 5/2003 | Brooks et al. |
| 2003/0148530 A1 | 8/2003 | Lauks |
| 2004/0227529 A1* | 11/2004 | Brooks ............... B01J 19/0093 324/693 |
| 2005/0114041 A1* | 5/2005 | Gawad ............... G01N 15/1056 702/29 |
| 2005/0118705 A1 | 6/2005 | Rabbitt et al. |
| 2006/0062074 A1 | 3/2006 | Gundersen et al. |
| 2008/0221805 A1 | 9/2008 | Andrews |
| 2009/0212788 A1 | 8/2009 | Patterson |
| 2010/0006441 A1 | 1/2010 | Renaud et al. |
| 2010/0025246 A1 | 2/2010 | Cho et al. |
| 2010/0088039 A1 | 4/2010 | Yang et al. |
| 2011/0080181 A1 | 4/2011 | Sato et al. |
| 2011/0162439 A1 | 7/2011 | Ayliffe |
| 2011/0275111 A1 | 11/2011 | Pettigrew et al. |
| 2011/0279130 A1 | 11/2011 | Reccius et al. |
| 2012/0084022 A1* | 4/2012 | Giovangrandi ........... G01F 1/58 702/45 |
| 2012/0142032 A1 | 6/2012 | Morgan et al. |
| 2012/0168309 A1 | 7/2012 | Heikenfeld |
| 2013/0085680 A1 | 4/2013 | Arlen et al. |
| 2013/0154671 A1 | 6/2013 | Lee et al. |
| 2013/0167621 A1 | 7/2013 | Lin et al. |
| 2013/0193003 A1 | 8/2013 | Reed et al. |
| 2013/0252234 A1 | 9/2013 | Nassef et al. |
| 2013/0258318 A1 | 10/2013 | Ayliffe |
| 2013/0267835 A1 | 10/2013 | Edwards |
| 2013/0313113 A1 | 11/2013 | Koser |
| 2014/0004501 A1 | 1/2014 | Talebpour et al. |
| 2014/0014509 A1 | 1/2014 | Yan |
| 2014/0021105 A1* | 1/2014 | Lee ................. G01N 27/44756 209/214 |
| 2014/0284221 A1 | 9/2014 | Liu et al. |

FOREIGN PATENT DOCUMENTS

| | | |
|---|---|---|
| CN | 102460114 | 5/2012 |
| CN | 102460137 | 5/2012 |
| JP | 2013015498 A | 1/2013 |
| TW | 200305717 A | 11/2003 |
| TW | 201224447 A | 6/2012 |
| WO | WO-2012064878 | 5/2012 |
| WO | WO-2012110922 | 8/2012 |
| WO | WO-2013117233 | 8/2013 |
| WO | WO-2014178827 | 11/2014 |
| WO | WO-2015116083 | 8/2015 |

OTHER PUBLICATIONS

Cheng, X. et al., "Cell detection and counting through cell lysate impedance spectroscopy in microfluidic devices." Lab on a Chip 7, No. 6 (2007): 746-755.

Chin, et al., "Low-cost microdevices for point-of-care testing." In Point-of-care Diagnostics on a chip, pp. 3-21. Springer Berlin Heidelberg, 2013.

Claudel, J. et al., "Microfluidic biosensor for single cell high speed flow impedance spectroscopy." In Proceedings of the 8th International Conference on Sensing Technology, pp. 343-347. 2014.

International Search Report/Written Opinion, dated May 19, 2015, PCT Patent Application No. PCT/US2015/013825.

International Search Report/Written Opinion, dated Oct. 27, 2014, PCT Patent Application No. PCT/US2014/013748.

International Search Report/Written Opinion, dated May 21, 2015. PCT Patent Application No. PCT/US2015/013854.

Impedance Spectroscopy Flow Cytometry: On-Chip Label-Free Cell Differentiation, Karen Cheung, ISAC Cytometry Part A 65A: 12-132, 2005.

Daniel Spencer et al: "Positional dependence of particles in microfludic impedance cytometry", Lab on a Chip, vol. 11, No. 7, Jan. 1, 2011 (Jan. 1, 2011), p. 1234, XP055125402, ISSN: 1473-0197, DOI: 10.1039/c11c20016j * Abstract, p. 1236, column 2: figures 1, 4 *.

Karen Cheung, Shady Gawad, and Philippe Renaud, "Impedance Spectroscopy Flow Cytometry: On-Chip Labe-Free Cell Differentiation", ISAC Cytometry Part 1 65A, 2005.

Minerick, A.R., et al. "Manipulation and characterization of red blood cells with alternating current fields in microdevices". Nov. 6, 2003, Electrophoresis, 24(21), pp. 3703-3717.

* cited by examiner

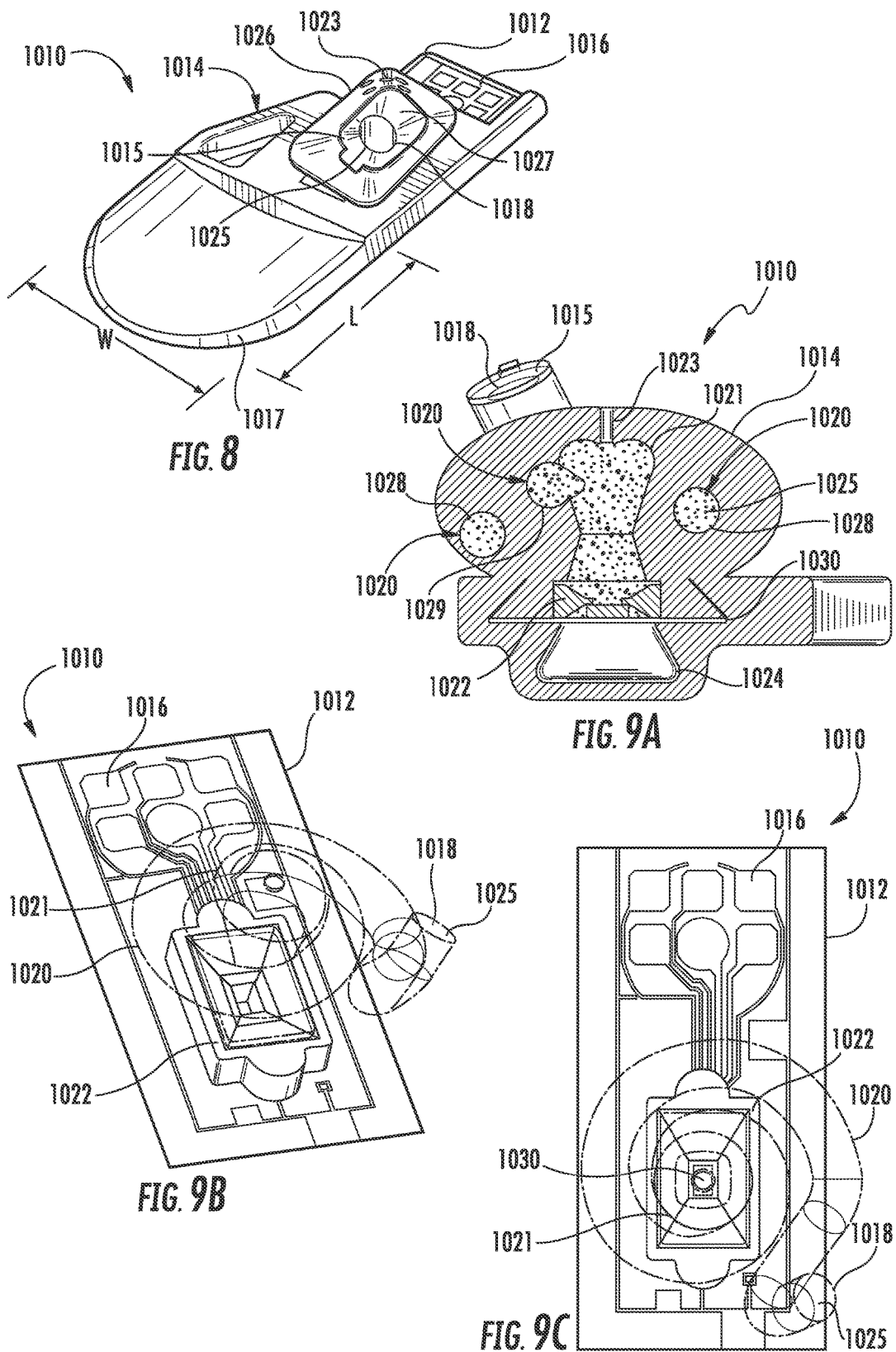

IMPEDANCE TESTING WITH ALTERNATING CURRENT FREQUENCY CONTROL

CROSS-REFERENCE TO RELATED APPLICATION

This application is a U.S. National Stage Application of International Patent Application No. PCT/US2015/013854, filed on Jan. 30, 2015, and entitled "IMPEDANCE TESTING WITH ALTERNATING CURRENT FREQUENCY CONTROL," which claims priority to International Patent Application No. PCT/US2014/013748, filed on Jan. 30, 2014, and entitled "MICROFLUIDIC SENSING DEVICE", hereby incorporated by reference in its entirety.

BACKGROUND

Fluid samples, such as blood samples, are frequently taken and analyzed for clinical diagnostics to identify disease and other health related issues. For such diagnostics, many different tests are performed on the fluid, requiring multiple different fluid samples. For example, such fluid testing frequently involves identification of the size of the cells or particles and identification of the number of such cells or particles. To perform the many different tests often requires multiple different fluid testing systems. Such existing fluid testing systems, such as benchtop testing systems, are large, cumbersome and difficult to use.

BRIEF DESCRIPTION OF THE DRAWINGS

FIG. 8 is a perspective view of an example cassette.

FIG. 9A is a sectional view of the cassette of FIG. 8 with a modified exterior.

FIG. 9B is a perspective view of the cassette of FIG. 9A with portions omitted or shown transparently.

FIG. 9C is a top view of the cassette of FIG. 9A with portions omitted or shown transparently.

DETAILED DESCRIPTION OF EXAMPLES

Figure 1:
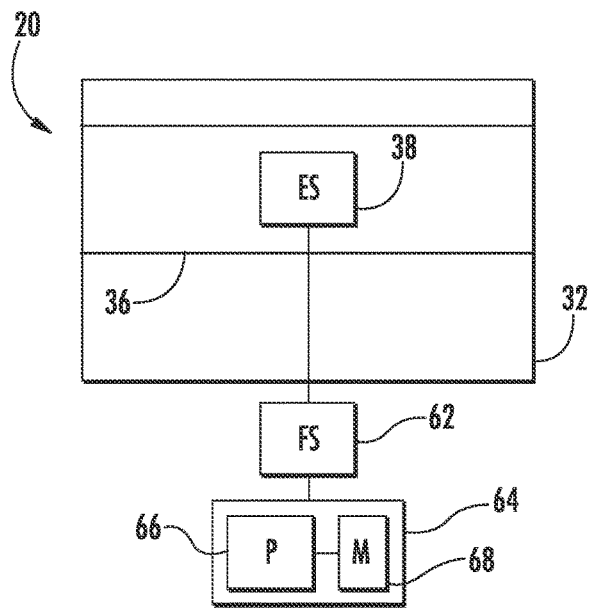
FIG. 1 is a schematic diagram of an example fluid testing system.

FIG. 1 schematically illustrates an example fluid testing system 20. As will be described hereafter, fluid testing system 20 provides a single platform to perform multiple different tests upon a single fluid sample. Because testing system 20 produces data for multiple different characteristics or parameters of the fluid being tested using a single fluid sample, system 20 allows such testing and diagnostics performed with a single testing system. Moreover, testing system 20 reduces a number of fluid samples or blood samples that must be taken and reduces the amount of potentially hazardous medical waste resulting from such testing.

Fluid testing system 20 comprises a substrate 32, microfluidic channel 36, electric sensors 38, frequency source 62 and frequency controller 64. Channel 36 comprises a fluidic channel or passage to direct and guide fluid of a fluid sample being tested. In one implementation, channel 36 is formed within a substrate of the microfluidic chip and extends from an inlet(not shown) to direct portions of the fluid sample across electric sensors 38. In one implementation, channel 36 directs fluid back to the reservoir of the microfluidic chip for circulating fluid. In another implementation, microfluidic channel 36 directs fluid back to a discharge reservoir or discharge port. In yet another implementation, channel 36 extends to other fluid destinations.

Electric sensor 38 comprises a micro-fabricated device formed upon a substrate 32 within channel 36. In the example illustrated, sensor 38 comprises a micro-device that is designed to output electrical signals or cause changes in electrical signals that indicate and measure properties, parameters or characteristics of the fluid and/or cells/particles of the fluid passing through channel 36. In the example illustrated, sensor 38 is used as an electric sensor. The electric sensors outputs signals which, based upon changes in the electrical signal, directly reflects the electrical impedance brought about by differently sized particles or cells flowing through channel. In one implementation, sensor 38 comprises an electrically charged electrode and an electrically grounded electrode formed within or integrated within a surface of channel 36. In one implementation, electric sensor 38 outputs signals indicating a number or quantity of cells or particles opposite to sensor 38 or passing across sensor 38 at any moment in time. electric sensor 38 outputs signals indicating characteristics of such individual cells or particles, such as a size of a cell or particle or the like.

Frequency source 62 comprises at least one source of different non-zero frequencies of alternating current. In one implementation, frequency source 62 comprises an individual frequency source dedicated for individual electric sensor 38. In another implementation, frequency source 62 comprises a single frequency source which selectively applies different non-zero frequencies of alternating current to the different electric sensors 38 or which concurrently supplies different non-zero frequencies of alternating current to the different electric sensors 38.

In one implementation, frequency source 62 comprises a direct digital synthesizer which comprises a frequency reference such as a crystal or surface acoustic wave (SAW) oscillator, a numerically controlled oscillator and a digital to analog converter. In another implementation, frequency source 62 comprises an analog or phase-locked loop (PLL) frequency source. In one implementation, frequency source 62 is designed so as to apply a first lower non-zero frequency of alternating current to electric sensor 38 to facilitate determination of the size of individual cells and to apply a second higher non-zero frequency of alternating current to the electric sensor 38 to facilitate other properties. In one implementation, frequency source 62 is designed to apply different non-zero frequencies to facilitate counting of the number of cells or particles passing across each of sensors 38.

Frequency controller 64 controls the application of the different non-zero frequencies of alternating current to electric sensors 38. In one implementation, frequency controller 64 facilitates user selection of the different non-zero frequencies of alternating current applied to electric sensor 38. Frequency controller 64 comprises processing unit 66 and memory 68. Processing unit follows instructions contained in memory 68 to output control signals directing the operation of frequency source 62. For purposes of this application, the term "processing unit" shall mean a presently developed or future developed processing unit that executes sequences of instructions contained in a memory. Execution of the sequences of instructions causes the processing unit to perform actions such as generating control signals. The instructions may be loaded in a random access memory (RAM) for execution by the processing unit from a read only memory (ROM), a mass storage device, or some other persistent storage or non-transitory computer-readable medium containing program logic or logic encodings. In other implementations, hard wired circuitry may be used in place of or in combination with machine readable instructions to implement the functions described. For example, controller 64 may be embodied as part of application-specific integrated circuits (ASICs). Unless otherwise specifically noted, the controller 64 is not limited to any specific combination of hardware circuitry and machine readable instructions, nor to any particular source for the instructions executed by the processing unit.

In one implementation, controller 64 automatically dynamically adjusts the frequency of alternating current being applied to electric sensor 38 based upon real time or ongoing performance of electric sensor 38 to improve upon performance system 20. For example, in one implementation, controller 64 outputs control signals that apply a first non-zero frequency of alternating current to the electric sensor 38. Based upon signals received from electric sensor 38 during the application of the first non-zero frequency of alternating current, controller 64 adjusts the value of the subsequently applied frequency of alternating current applied to electric sensor 38. Controller 64 outputs control signals such that frequency source 62 applies a second non-zero frequency of alternating current to the electric sensor 38, wherein a value of the second non-zero frequency of alternating current applied by frequency source 62 to the electric sensor 38 is based upon signals received from the electric sensor 38 during the application of the first non-zero frequency of alternating current.

In one implementation, controller 64 selectively applies different non-zero frequencies of alternating current to perform different tests upon the fluid sample. As a result of controller 64 causing frequency source 62 to apply different non-zero frequencies of alternating current to the electric sensor 38, the electric sensor 38 performs different tests, outputting different signals that may indicate different properties or characteristics of the fluid, or cells contained therein. Such different tests are performed on a single fluid sample on a single fluid testing platform without the fluid sample having to be transferred from one testing device to another. As a result, integrity the fluid sample is maintained, the cost and complexity of performing the multiple different tests is reduced and the amount of potentially bio-hazardous waste is also reduced.

Figure 2:
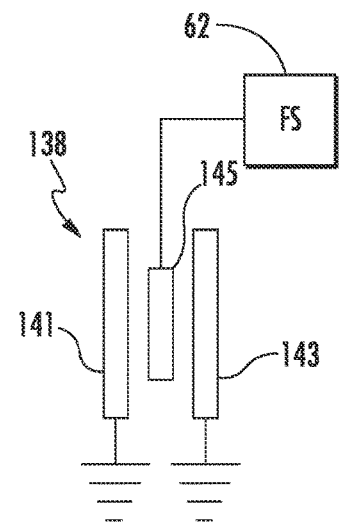
FIG. 2 is a schematic diagram of an example electric sensor of the fluid testing system of FIG. 1.

FIG. 2 schematically illustrates electric sensor 138, an example of at least one of electric sensors 38. As shown by FIG. 2, electric sensor 138 comprises low side electrodes 141, 143 and charged or active high side electrode 145. Active high side electrode 145 is sandwiched between low side electrodes 143. Low side electrodes 143 share active high side electrode 145, wherein an electrical field is formed between active high side electrode 145 and each of the two low side electrodes 141, 143. In the illustrated example, low side electrodes 141, 143 or electrically grounded. In another implementation, low side electrodes may not be grounded, but may be floating low side electrodes. As fluid flows across the electrodes 141, 143, 145 and through the electrical field, the particles or cells within the fluid impact the impedance of the electrical field. This impedance is sensed to identify characteristics of the cells or particles.

As further shown in FIG. 2, frequency source 62 is electrically coupled or connected to active electrode 145 to apply a controlled non-zero frequency of alternating current to active high side electrode 145. In other implementations, electric sensor 38 has a different configuration or design, wherein at least one electric field is generated which is perturbed in response to cells passing through the electric field.

Figure 3:
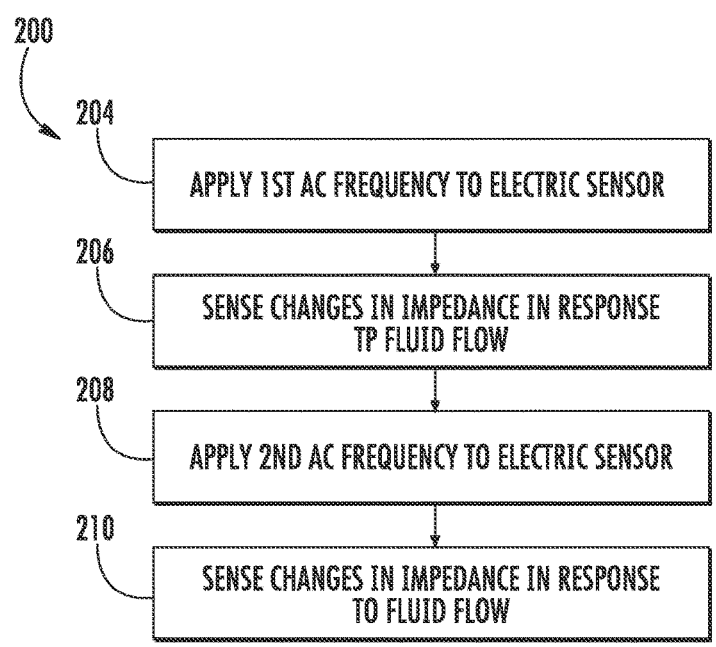
FIG. 3 is a flow diagram of an example method for fluid testing.

FIG. 3 is a diagram of an example method 200 for sensing different characteristics of cells or particles of the fluid using an electric sensor. In one implementation, method 200 is carried out by system 20 described above with respect to FIG. 1. As indicated by block 204, controller 64 outputs control signals, following constructions contain a memory 68, to direct frequency source 62 to apply a first nonzero frequency of alternating current to electric sensor 38. As a result, a first electric field is established within fluid channel 36.

As indicated by block 206, processor 66 receives signals indicating changes in impedance that occur in response to the flow of the fluid sample or blood sample through the first electric field of electric sensor 38 produced by the first frequency of alternating current being applied to the active electrode or the active electrodes of electric sensor 38.

Processor 66 utilizes such signals to estimate or determine a first characteristic of the fluid flowing through the electric field. This first characteristic is stored in memory 68 and/or is forwarded for further analysis or diagnosis.

As indicated by block 208, controller 64 outputs control signals, following instructions contained in memory 68, to direct frequency source 62 to apply a second nonzero frequency of alternating current, different than the first nonzero frequency of alternating current, to electric sensor 38. As a result, a second electric field is established within fluid channel 36.

As indicated by block 210, processor 66 receives signals indicating changes in impedance that occur in response to the flow of the fluid sample or blood sample through the second electric field of electric sensor 38. Processor 66 utilizes such signals to estimate or determine a second characteristic of the fluid flowing through the electric field, the second characteristic being different than the first characteristic. This second characteristic is stored in memory 68 and/or is forwarded for further analysis or diagnosis.

In one implementation, the first and second nonzero frequencies of alternating current applied to electric sensor 38 are selected so as to detect or respond to different characteristics of the fluid flowing across electric sensor 38. For example, in one implementation, the first non-zero frequency of alternating current is a low frequency that falls within a range to enhance the detection of the size of individual cells or particles contained within the fluid that align across electric sensor 38. In such an implementation, the second non-zero frequency of alternating current is a high frequency that falls within a higher range to enhance the detection of other characteristics of the individual cells. As a result, a larger amount of information about the individual cells is extracted using a single electric sensor 38 operated at different frequencies of alternating current. In one implementation, the first non-zero frequency of alternating current is at a frequency of N up to 10 MHz.

In yet other implementations, the first and second nonzero frequencies of alternating current are selected to enhance reliability during the counting of the individual cells or particles within the fluid flowing across electric sensor 38 during a particular window of time. By sensing impedance changes at multiple different nonzero frequencies of alternating current, results may be obtained that are less dependent upon the microfluidic design of channel 36 through which the cells flow. As a result, the greater tolerance error in the sorting and differentiating of cell types is obtained.

Figure 4:
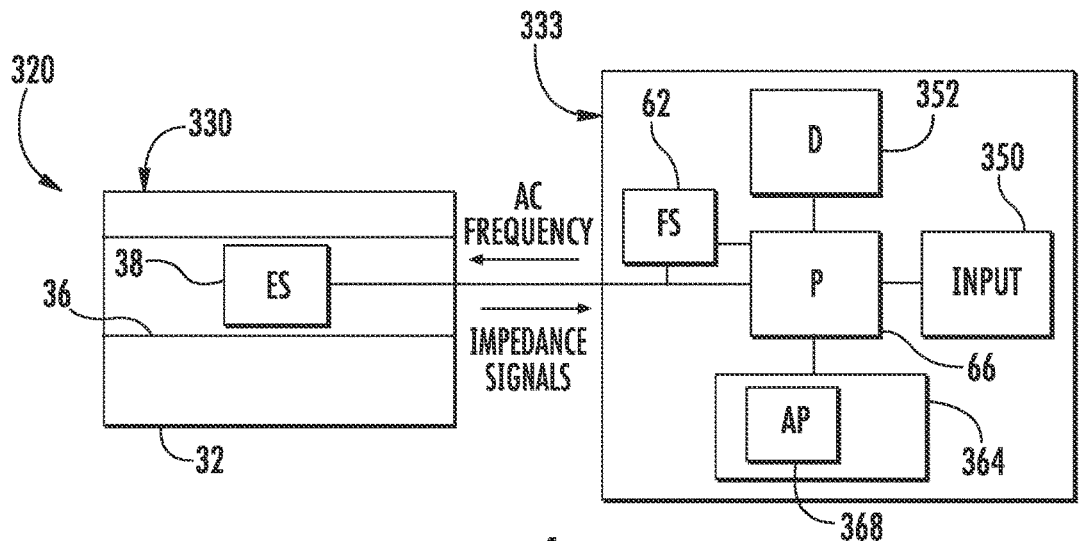
FIG. 4 is a schematic diagram of another example fluid testing system.

FIG. 4 schematically illustrates fluid testing system 320, an example implementation of fluid testing system 20. Fluid testing system 320 comprises fluid testing device 330 and analyzer 333. Fluid testing system 320 is similar to fluid testing system 20 except that fluid testing system 320 is additionally illustrated as comprising memory input 350, display 352 and memory 364. Those remaining elements or components of fluid testing system 320 which correspond to elements or components of fluid testing system 20 are numbered similarly.

Input 350 comprises a user interface by which a person may input commands, selection or data to processor 66. Examples of input 350 include, but are not limited to, a keyboard, a touchscreen (in one implementation a touchscreen of display 570), a touchpad, a mouse, a pushbutton or slider bar, a toggle switch, a microphone with associated speech recognition program and the like. In one implementation, input 350 facilitates input of different frequencies of alternating current corresponding to different tests to be run upon a fluid sample placed in channel 36.

Display 352 comprises a monitor or screen by which data is visually presented. In one implementation, display 352 facilitates a selection of different tests or of different nonzero frequencies of alternating current by user. In one implementation, display 352 comprise a touch screen which serves as input 350.

Memory 364 comprises a non-transitory computer readable medium. Memory 364 Is similar to memory 64 except that memory 364 is specifically illustrated as comprising application program module 368. Application program module 368 comprises machine readable instructions, code, programmed logic or logic encodings stored in memory 364 to direct interaction between system 320 and a user through input 350 and display 352. Application program 368 assists in caring out method 400 illustrated in FIG. 5.

Figure 5:
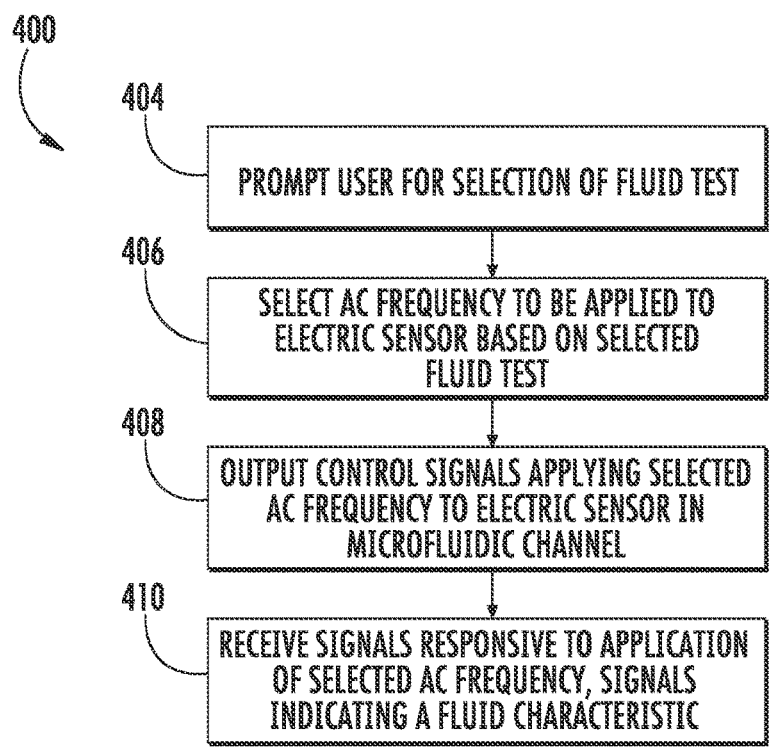
FIG. 5 is a flow diagram of another example method for fluid testing.

As indicated by block 404 of FIG. 5, application program module 368 directs processor 66 to prompt a user for selection of a particular fluid test to be carried out by system 320. In one implementation, application program module 368 causes processor 66 to display, for selection by user, different names of different tests or the characteristics or cell/particle parameters for selection. For example, processor 66 may display cell count, cell size or some other parameter for selection by the user using input 350.

In one implementation, prior to prompting a user for selection of a particular fluid test, module 368 direct processor 66 to carry out a check with the fluid testing device providing electric sensor 38 to determine or identify what fluid tests or what frequency ranges are available or for which the fluid testing device is capable of providing. In such an implementation, module 368 automatically eliminates those fluid tests that cannot be provided by the fluid testing device 330 from the list or menu of possible choices of fluid tests being presented to the user. In yet another implementation, module 368 presents a full menu of fluid tests, but notifies the user of those particular fluid tests that are not presently available or selectable given the current fluid testing device 330 connected to analyzer 333.

As indicated by block 406 in FIG. 5, based upon the received selection for the fluid test to be carried out, processor 66, following instructions contained in application program module 368, selects a value or values for the frequency of alternating current to be applied to the electric sensor 38. In one implementation, processor 66 identifies a particular frequency of alternating current to be applied. In another implementation, processor 26 identifies a particular range of frequencies which are to be applied to electric sensor 38. In another implementation, processor 26 identifies a plurality of different frequencies of alternating current that are to be sequentially applied to electric sensor 38 for carrying out the selected fluid test for the selected cell/particle parameters.

In another implementation, block 406 omitted, where application program module 368 causes processor 66 to display the different available frequencies or frequency ranges for testing that may be selected by user. For example, processor 66 may display multiple different available frequency ranges or may prompt the user to input or identify a particular frequency value. In such an implementation, the user directly inputs a frequency of alternating current, a range of frequencies of alternating current or a plurality of different or separate frequencies of alternating current to be applied during fluid testing to electric sensor 38. For example, module 368 may determine that accuracy of the results for the particular fluid test selected by a user in block 404 may be enhanced by specifically applying three different predetermined frequencies to electric sensor 38 for predefined periods of time and in a predefined order.

As indicated by block 408, application program module 368 directs processor 66 to output control signals causing frequency source 62 to apply the selected or identified frequency of alternating current (or the range or the multiple different values) to electric sensor 38 in microfluidic channel 36. As noted above, in one implementation, a single frequency is applied. In one implementation, a single varying frequency is applied, wherein the frequency may fluctuate within a predefined selected range of values. In yet another implementation, the plurality of different predefined frequencies of alternating current are sequentially applied during testing.

As indicated by block 410 in FIG. 5, analyzer 333 receives signals from electric sensor 38 responsive to the application of the selected frequency of alternating current, wherein the signals indicate or correspond to the characteristic or parameter of the fluid sample or blood sample being tested. As noted above, in one user selected fluid test, the changes in impedance reflected by the signals received from electric sensor 38 in response to the applied frequency of alternating current indicate the size of cells or particles of the fluid proximate electric sensor 38. In another user selected fluid test, the changes in impedance reflected by the signals received from electric sensor 38 in response to the applied frequency of alternating current indicate the number of cells or particles of the fluid proximate electric sensor 38. In yet other user selected fluid tests, the changes in impedance reflected by the signals received from electric sensor 38 in response to the applied frequency of alternating current indicate other aircrew six are parameters of the cells or particles. By automatically identifying those particular frequencies of alternating current most suitable for the particular parameters being tested and then automatically applying the identified frequency or frequencies to electric sensor 38 during the test, fluid testing system 320 provides more accurate and reliable results.

Figure 6A:
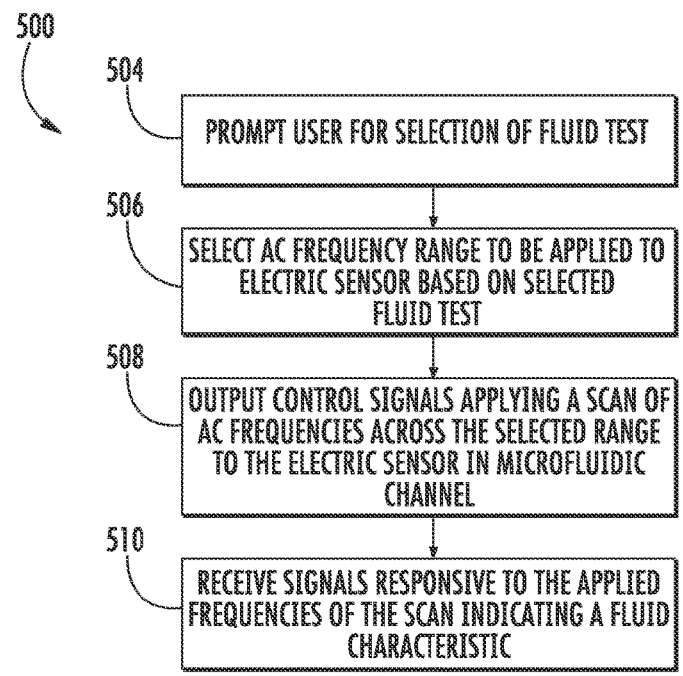
FIG. 6A is a flow diagram of another example method for fluid testing.

FIG. 6A is a flow diagram of method 500, another example of a method that may be carried out by fluid testing system 320 when testing a fluid sample. In one implementation, fluid testing system 320 prompts a user to select different modes of operation, carrying out either method 400 shown and described with respect to FIG. 5 or method 500 described hereafter. Method 500 is similar to method 400 except that method 500 utilizes a scan of different frequencies of alternating current across a range or spectrum of frequencies when testing for an individual parameter characteristic.

As indicated by block 504, application program module 368 directs processor 66 to prompt a user for selection of a particular fluid test to be carried out by system 320. In one implementation, application program module 368 causes processor 66 to display, for selection by user, different names of different tests or the characteristics or cell/particle parameters for selection. For example, processor 66 may display cell count, cell size or some other parameter for selection by the user using input 350.

In one implementation, prior to prompting a user for selection of a particular fluid test, module 368 direct processor 66 to carry out a check with the fluid testing device providing electric sensor 38 to determine or identify what fluid tests or what frequency ranges are available or for which the fluid testing device is capable of providing. In such an implementation, module 368 automatically eliminates those fluid tests that cannot be provided by the fluid testing device 330 from the list or menu of possible choices of fluid tests being presented to the user. In yet another implementation, module 368 presents a full menu of fluid tests, but notifies the user of those particular fluid tests that are not presently available or selectable given the current fluid testing device 330 connected to analyzer 333.

As indicated by block 506 in FIG. 6A, based upon the received selection for the fluid test to be carried out, processor 66, following instructions contained in application program module 368, selects a range of frequencies of alternating current which is to be crossed or covered during testing with the electric sensor 38. In contrast to the range described above with respect to block 406 which is a range that provides tolerance for fluctuations in the applied frequency of alternating current, the range identified and selected in block 506 is a range across which multiple different frequency of alternating current are to be applied to electric sensor 38 according to a predefined scan profile. The range in block 508 identifies the endpoints for a series of different frequencies of alternating current to be applied to electric sensor 38 during testing. The scan profile indicates the specific AC frequency values between the endpoints of the range and their timing of their application to electric sensor 38.

In one implementation or user selected mode of operation, processor 66 identifies the particular range most suited for the fluid test selected by the user in block 504, wherein the scan profile is a default profile, being the same for each of the different ranges. In another implementation or user selected mode of operation, processor 66 automatically identifies the particular scan range most suited for the selected fluid test, wherein the user is prompted to select a scan profile. In another implementation or user selected mode of operation, processor 66, following instructions contained in module 368, automatically identifies not only the most appropriate range for the particular fluid test selected by the user in block 504, but also the particular scan profile for the particular range for the particular fluid test selected by the user in block 504. In still another implementation or user selectable mode of operation, the user is prompted to select a particular scan profile, wherein processor 66 identifies the most appropriate scan range, given the selected scan profile for the particular selected fluid test. In one implementation, memory 364, or a remote memory, contains a lookup table which identifies different scan ranges in different scan profiles for different available or selectable fluid tests or fluid/sell/particle parameters for which a fluid test may be performed.

Figure 6B:
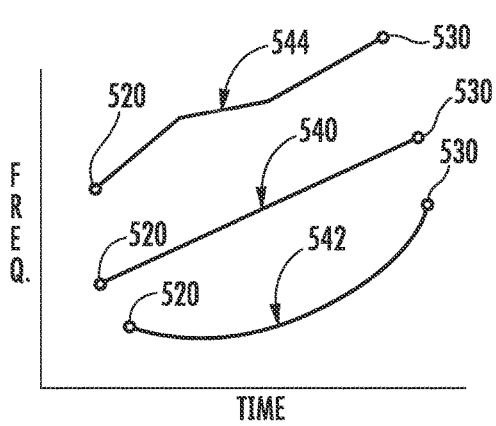
FIG. 6B is a diagram illustrating example continuous alternating frequency scan profiles.
Figure 6C:
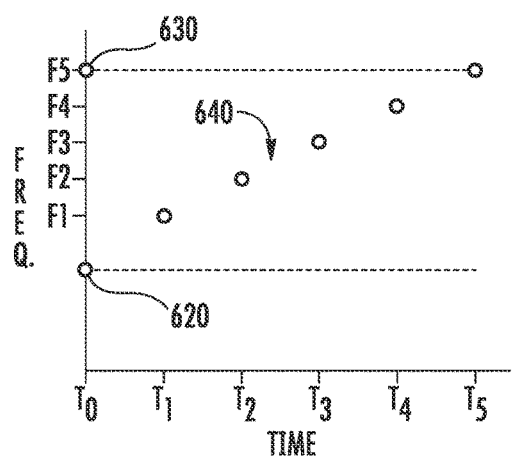
FIG. 6C is a diagram illustrating an example intermittent alternating frequency scan profile.

FIGS. 6B and 6C illustrate various examples of different scan profiles. As shown in FIG. 6B, in one implementation, the application of different frequencies between endpoints 520, 530 of the range may be in a continuous fashion ramping up or ramping down during the predefined what period of time in an unceasing, uninterrupted, unbroken or constant manner. As indicated by the example frequency scan profile 540, in one user selected mode of operation, system 320 linearly ramps up between endpoints 520, 530. As indicated by example frequency scan profile 542, in one user selected mode of operation, system 320 changes the applied frequency in a continuous arcuate manner. As indicated by example frequency scan profile 544, in one user selected mode of operation, system 320 changes the applied frequency in a continuous manner through multiple intermediate linear ramping segments.

In yet another mode of operation or in another implementation, as illustrated by FIG. 6C, the range identifies upper and lower boundaries, wherein fluid testing system 333 applies a series of different frequencies of alternating current, between the endpoints 620, 630, at predefined times spaced from one another. For example, at time T0, a frequency of F0 is applied. At time T1, a frequency of F1 is applied. At time T2, a frequency of F2 is applied and so on.

Although FIG. 6C illustrates an example scan profile 640 in which five different frequency of alternating current between the endpoints 620, 630 are applied, in other implementations or in other user selectable modes, a greater or fewer of such different frequencies may be applied. Although FIG. 6C illustrates the application of the different frequencies in a periodic fashion apart in time by substantially uniform periods of time, in other implementations or in other user selectable modes, the application of the different frequencies may occur at non-uniformly spaced intervals. Although FIG. 6C illustrates the application of the different frequencies pursuant to a linear function, wherein the value of the applied frequency of alternating current eight each of the distinct times is incrementally increased in a uniform fashion (the jump between F1 and F2 is equal to the jump between F2 and F3, and so on), in other implementations or in other user selectable modes, the application of different frequencies may be incremented in a non-uniform fashion or nonlinearly (the jump between F1 and F2 is different than the jump between F2 and F3 and so on).

In another implementation, block 506 omitted, where application program module 368 causes processor 66 to display the different frequency ranges for testing that may be selected by user. For example, in one implementation, processor 66 displays multiple different available frequency ranges or may prompt the user to input or identify a particular frequency range. In one implementation, processor 66 identifies a recommended plurality of alternatives with respect to a frequency range most suited for the selected fluid test for the particular fluid or cell characteristics being tested, wherein processor 66 then prompts the user to make a choice from the system recommended subset of alternatives. For example, out of a set of scan ranges A, B, C, D, E, and F, processor 66 may determine that ranges C, D and E are most appropriate for the particular fluid test or particular fluid characteristic being tested. User 66 and then allows the user to choose from ranges C, D and E.

In one implementation, processor 66 also displays for selection or prompts a user to input the scan profile for the frequencies, such as whether scan profile such as scan profile 540, 542, 544, 640 or another scan profile are to be followed. In one implementation, processor 66 recommends particular scan profiles, but allows the user to choose. In one implementation, processor 66 presents just the recommended scan profiles from which the user may choose. In such implementations, the user directly inputs the scan range of frequencies and the scan profile of alternating current to be applied during fluid testing to electric sensor 38.

As indicated by block 508, application program module 368 directs processor 66 to output control signals causing frequency source 62 to apply the selected or identified scan frequency range and scan profile to electric sensor 38 in microfluidic channel 36.

As indicated by block 510 in FIG. 6A, analyzer 333 receives signals from electric sensor 38 responsive to the application of the selected scan frequency range and scan profile, wherein the signals indicate or correspond to the characteristic or parameter of the fluid sample or blood sample being tested. As noted above, in one user selected fluid test, the changes in impedance reflected by the signals received from electric sensor 38 in response to the applied different frequencies, within the scan range and according to the scan profile, indicate the size of cells or particles of the fluid proximate electric sensor 38. In another user selected fluid test, the changes in impedance reflected by the signals received from electric sensor 38 in response to the applied different frequencies within the scan range and according to the scan profile indicate the number of cells or particles of the fluid proximate electric sensor 38. In yet other user selected fluid tests, the changes in impedance reflected by the signals received from electric sensor 38 in response to the applied frequency within the scan range and according to the scan profile indicate other characteristics or parameters of the cells or particles. By automatically identifying those particular scan ranges and, in some implementations scan profiles, most suitable for the particular parameters being tested and then automatically applying the identified scan frequency range and scan profile to electric sensor 38 during the test, fluid testing system 320 provides more accurate and reliable results.

Figure 7:
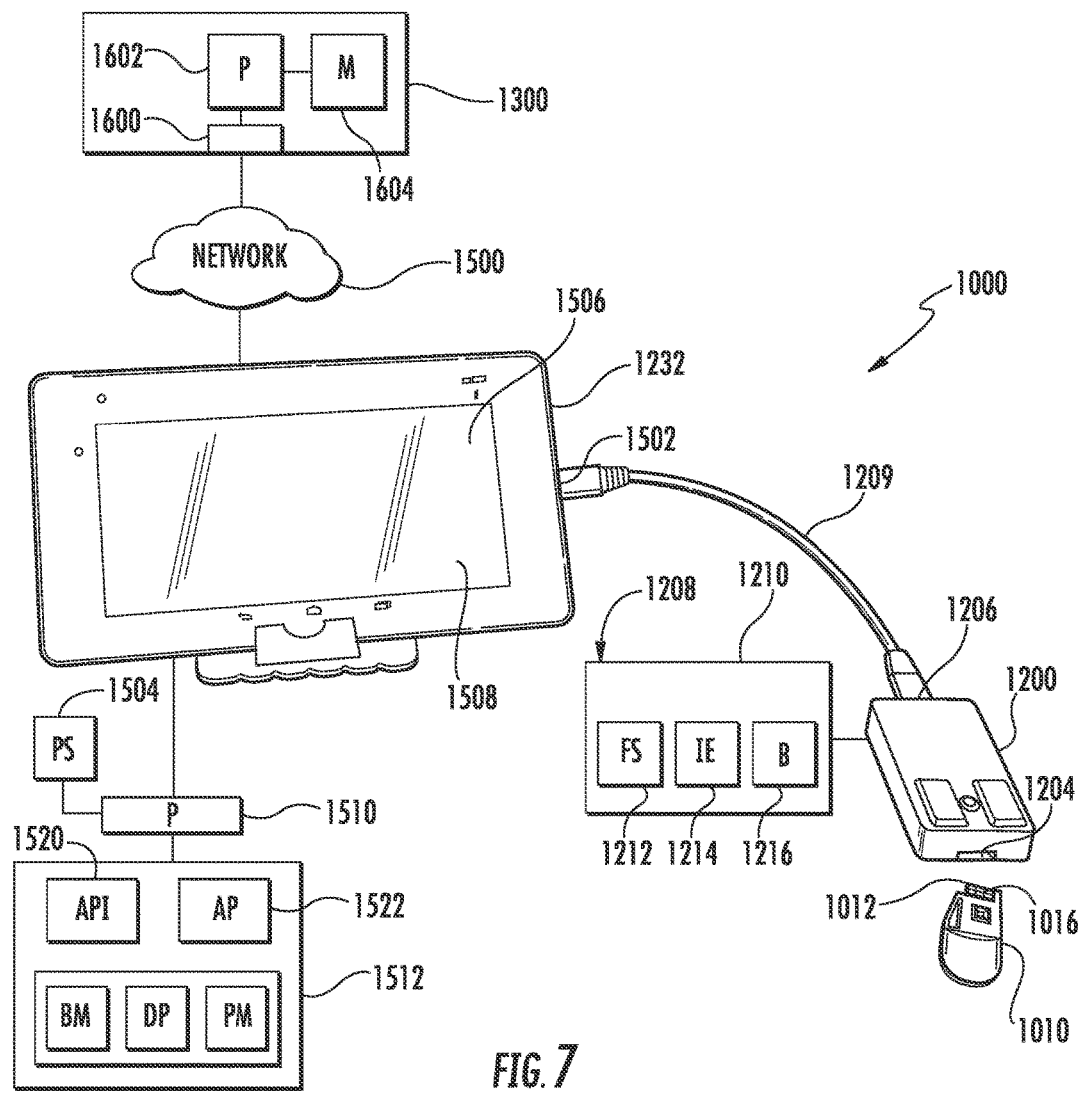
FIG. 7 is a schematic diagram of another example fluid testing system.

FIG. 7 illustrates an example microfluidic diagnostic or testing system 1000. System 1000 comprises a portable electronic device driven, impedance-based system by which samples of fluid, such as blood samples, are analyzed. For purposes of this disclosure, the term "fluid" comprises the analyte in or carried by the fluid such as a cell, particle or other biological substance. The impedance of the fluid refers to the impedance of the fluid and/or any analyte in the fluid. System 1000, portions of which are schematically illustrated, comprises microfluidic cassette 1010, cassette interface 1200, mobile analyzer 1232 and remote analyzer 1300. Overall, microfluidic cassette 1010 receives a fluid sample and outputs signals based upon sensed characteristics of the fluid sample. Interface 1200 serves as an intermediary between mobile analyzer 1232 and cassette 1010. Interface 1200 removably connects to cassette 1010 and facilitates transmission of electrical power from mobile analyzer 1232 to cassette 1010 to operate pumps and sensors on cassette 1010. Interface 1200 further facilitates control of the pumps and sensors on cassette 1010 by mobile analyzer 1232. Mobile analyzer 1232 controls the operation cassette 1010 through interface 1200 and receive data produced by cassette 1010 pertaining to the fluid sample being tested. Mobile analyzer 1232 analyzes data and produces output. Mobile analyzer 1232 further transmits processed data to remote analyzer 1300 for further more detailed analysis and processing. System 1000 provides a portable diagnostic platform for testing fluid samples, such as blood samples.

Figure 10A:
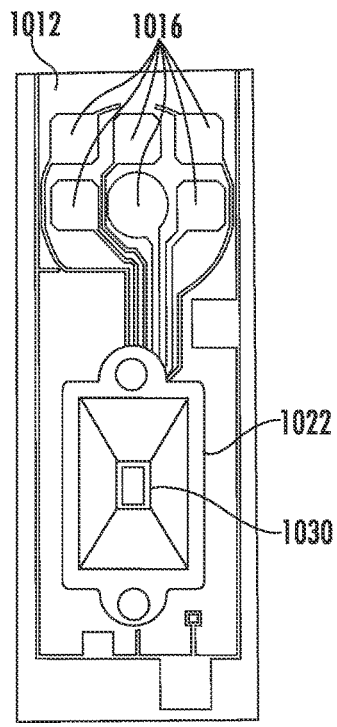
FIG. 10A is a top view of an example cassette board supporting an example microfluidic cassette and funnel
Figure 10B:
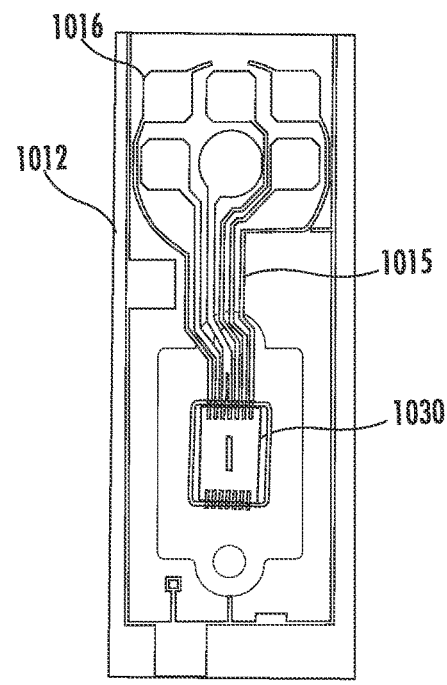
FIG. 10B is a bottom view of the cassette board of FIG. 10A.

FIGS. 8-21 illustrate microfluidic cassette 1010 in detail. As shown by FIGS. 8-10, cassette 1010 comprises cassette board 1012, cassette body 1014, membrane 1015 and microfluidic chip 1030. Cassette board 1012, shown in FIGS. 10A and 10B, comprises a panel or platform in which or upon which fluid chip 1030 is mounted. Cassette board 1012 comprises electrically conductive lines or traces 1015 which extend from electrical connectors of the microfluidic chip 1030 to electrical connectors 1016 on an end portion of cassette board 1012. As shown in FIG. 8, electrical connectors 1016 are exposed on an exterior cassette body 1014. As shown by FIG. 7, the exposed electrical connectors 1016 are designed to be inserted into interface 1200 so as to be positioned in electrical contact with corresponding electrical connectors within interface 1200, providing electrical connection between microfluidic chip 1030 and cassette interface 1200.

Cassette body 1014 partially surrounds cassette board 1012 so as to cover and protect cassette board 1012 and microfluidic chip 1030. Cassette body 1014 facilitates manual manipulation of cassette 1010, facilitating manual positioning of cassette 1010 into releasable interconnection with interface 1200. Cassette body 1014 additionally positions and seals against a person's finger during the acquisition of a fluid or blood sample while directing the received fluid sample to microfluidic chip 1030.

In the example illustrated, cassette body 1014 comprises finger grip portion 1017, sample receiving port 1018, residence passage 1020, sample holding chamber 1021, chip funnel 1022, vent 1023 and discharge reservoir 1024. Finger grip portion 1017 comprises a thin portion of body 1014 opposite to the end of cassette 1010 at which electrical connectors 1016 are located. Finger grip portion 1017 facilitates gripping of cassette 1010 in connection or insertion of cassette 1010 into a receiving port 1204 of cassette interface 1200 (shown in FIG. 7). In the example illustrated, finger grip portion 1017 has a width W of less than or equal to 2 inches, a length L of less than or equal to 2 inches and a thickness of less than or equal to 0.5 inches.

Sample receiving port 1018 comprises an opening into which a fluid sample, such as a blood sample, is to be received. In the example illustrated, sample receiving port 1018 has a mouth 1025 that is formed on a top surface 1027 of an elevated platform or mound 1026 that extends between finger grip portion 1017 and the exposed portion of cassette board 1012. Mound 1026 clearly identifies the location of sample receiving port 1018 for the intuitive use of cassette 1010. In one implementation, the top surface 1027 is curved or concave to match or approximately match the lower concave surface of a finger of a person so as to form an enhanced seal against the bottom of the person's finger from which the sample is taken. Capillary action pulls in blood from the finger which forms the sample. In one implementation, the blood sample is of 5 to 10 microliters. In other implementations, port 1018 is located at alternative locations or mound 1026 is omitted, for example, as depicted in FIG. 9A. Although FIG. 9A illustrates cassette 1010 having a slightly different outer configuration for cassette body 1014 as compared to body 1014 shown in FIG. 8, wherein the cassette body 1014 shown in FIG. 9A omits mound 1026, those remaining elements or components shown in FIGS. 8 and 9A are found in both of the cassette bodies shown in FIGS. 8 and 9A.

As shown by FIGS. 9A-9C, residence passage 1020 comprises a fluid channel, conduit, tube or other passage extending between sample input port 1018 and sample holding chamber 1021. Residence passage 1020 extends between sample input port 1018 and sample holding chamber 1021 in a tortuous fashion, an indirect or non-linear fashion full of twists and turns, to lengthen the time for a received sample, input through sample input port 1018, to travel or flow to chip 1030. Residence passage 1018 provides a volume in which the fluid sample being tested and a fluid reagent may mix prior to reaching chip 1030. In the example illustrated, residence passage 263 is circuitous, comprising a circular or helical passage winding in the space of cassette body 1012 between port 1018 and chip 1030. In another implementation, residence passage thousand 20 twists and turns, zigzags, snakes, serpentines and/or meanders in a zigzag fashion within the space between sample input port 1018 and chip 1030.

In the example illustrated, residence passage 1020 extends in a downward direction towards microfluidic chip 1030 (in the direction of gravity) and subsequently extends in an upward direction away from microfluidic chip 1030 (in a direction opposite to that of gravity). For example, as shown by FIGS. 9A and 9B, upstream portions 1028 extend vertically below the downstream end portion 1029 of residence passage 1020 that is adjacent to and directly connected to sample holding chamber 1021. Although upstream portions receive fluid from input port 1018 before end portion 1029, end portion 1029 is physically closer to input port 1018 in a vertical direction. As a result, fluid flowing from the upstream portions flows against gravity to the downstream or end portion 1029. As described hereafter, in some implementations, residence passage 1020 contains a reagent 1025 which reacts with the fluid sample or blood sample being tested. In some circumstances, this reaction will produce residue or fallout. For example, a fluid sample such as blood that has undergone lysis will have lysed cells or lysate. Because end portion 1029 of residence passage 1020 extends above upstream portions 1028 of residence passage 1020, such residue or fallout resulting from the reaction of the fluid sample with reagent 1025 settles out and is trapped or retained within such upstream portions 1028. In other words, the amount of such residue or fallout passing through residence passage 1020 to microfluidic chip 1030 is reduced. In other implementations, residence passage 1020 extends in a downward direction to sample holding chamber 1021 throughout its entire course.

Sample holding chamber 1021 comprises a chamber or internal volume in which the fluid sample or blood sample being tested collects above chip 1030. Chip funnel 1022 comprises a funneling device that narrows down to chip 1030 so as to funnel the larger area of chamber 1021 to the smaller fluid receiving area of chip 1030. In the example illustrated, sample input port 1018, residence passage 1020, sample holding chamber 1021 and chip funnel 1022 form an internal fluid preparation zone in which a fluid or blood sample may be mixed with a reagent before entering chip 1030. In one implementation, the fluid preparation zone has a total volume of 20 to 250 µL. In other implementations, the fluid preparation zone provided by such internal cavities may have other volumes.

As indicated by stippling in FIG. 9A, in one implementation, cassette 1010 is prefilled with a fluid reagent 1025 prior to insertion of a sample fluid to be tested into port 1018. Fluid reagent 1025 comprises a composition that interacts with the fluid to be tested, enhancing the ability of microfluidic chip 130 to analyze a selected characteristic or a group of selected characteristics of the fluid to be tested. In one implementation, fluid reagent 1025 comprises a composition to dilute the fluid being tested. In one implementation, fluid reagent 1025 comprises a composition to perform lysis on the fluid or blood being tested. In yet another implementation, fluid reagent 264 comprises a composition to facilitate tagging of selected portions of the fluid being tested. For example, in one implementation, fluid reagent 1025 comprises magnetic beads, gold beads or latex beads. In other implementations, fluid reagent 1025 comprises other liquid or solid compositions or liquids, distinct from the sample fluid to be tested, that interact with or that modify the sample fluid placed within sample input port 1018 prior to the sample fluid being received, processed and analyzed by microfluidic chip 1030.

Vents 1023 comprise passages communicating between sample holding chamber 1021 and the exterior of cassette body 1014. In the example illustrated in FIG. 8, vents 1023 extend through the side of mount 1026. Vents 1023 are sized small enough to retain fluid within sample holding chamber 1021 through capillary action but large enough so as to permit air within holding chamber 1021 to escape as holding chamber 1021 is filled with fluid. In one implementation, each of their vents has an opening or diameter of 50 to 200 micrometers.

Discharge reservoir 1024 comprises a cavity or chamber within body 1014 arranged to receive fluid discharged from chip 1030. Discharge reservoir 1024 is to contain fluid that has been passed through chip 1030 and that has been processed or tested. Discharge reservoir 1024 receives processed or tested fluid such that the same fluid is not tested multiple times. In the example illustrated, discharge reservoir 1024 is formed in body 1014 below chip 1030 or on a side of chip 1030 opposite to that of chip funnel 1022 and sample holding chamber 1021 such that chip 1030 is sandwiched between chip funnel 1022 and discharge reservoir 1024. In one implementation, discharge reservoir 1024 is completely contained within body 1014 and is inaccessible (but through the destruction of body 1014 such as by cutting, drilling or other permanent destruction or breaking of body 1014), locking the processed or tested fluid within body 112 for storage or subsequent sanitary disposal along with disposal of cassette 1010. In yet another implementation, discharge reservoir 1024 is accessible through a door or septum, allowing processed or tested fluid to be withdrawn from reservoir 1020 for further analysis of the tested fluid, for storage of the tested fluid in a separate container or for emptying of reservoir 1024 to facilitate continued use of cassette 1010.

In some implementations, microfluidic reservoir 1024 is omitted. In such implementations, those portions of the fluid samples or blood samples that have been tested are processed by microfluidic chip 1030 are recirculated back to an input side or input portion of microfluidic chip 1030. For example, in one implementation, microfluidic chip 1030 comprises a microfluidic reservoir which receives fluid through chip funnel 1022 on a input side of the sensor or sensors provided by microfluidic chip 1030. Those portions of a fluid sample or blood sample that have been tested are returned back to the microfluidic reservoir on the input side of the sensor or sensors of microfluidic chip 1030.

Membrane 1015 comprises an imperforate, liquid impermeable panel, film or other layer of material adhesively are otherwise secured in place so as to extend completely across and completely cover mouth 1025 of port 1018. In one implementation, membrane 1015 serves as a tamper indicator identifying if the interior volume of cassette 1010 and its intended contents have been compromised or tampered with. In implementations where the sample preparation zone of cassette 1010 has been prefilled with a reagent, such as reagent 1025 described above, membrane 1015 seals the fluid reagent 1025 within the fluid preparation zone, within port 1018, residence passage 1020, fluid holding chamber 1021 and chip funnel 1022. In some implementations, membrane 1015 additionally extends across vents 1023. Some implementations, membrane 1015 is additionally gas or air impermeable.

In the example illustrated, membrane 1015 seals or contains fluid reagent 1025 within cassette 1010 at least until the fluid sample is to be deposited into sample input port 1018. At such time, membrane 1015 may be peeled away, torn or punctured to permit insertion of the fluid sample through mouth 1018. In other implementations, membrane 1015 may comprises septum through which a needle is inserted to deposit a fluid or blood sample through mouth 1018. Membrane 1015 facilitates pre-packaging of fluid reagent 1025 as part of cassette 1010, wherein the fluid agent 1025 is ready for use with the subsequent deposits of the fluid sample to be tested. For example, a first cassette 1010 containing a first fluid reagent 1025 may be predesigned for testing a first characteristic of a first sample of fluid while a second cassette 1010 containing a second fluid reagent 1025, different than the first fluid reagent 1025, may be predesigned or pre-manufactured for testing a second characteristic of a second sample of fluid. In other words, different cassettes 1010 may be specifically designed for testing different characteristics depending upon the type or a quantity of fluid reagent 1025 contained therein.

Figure 11:
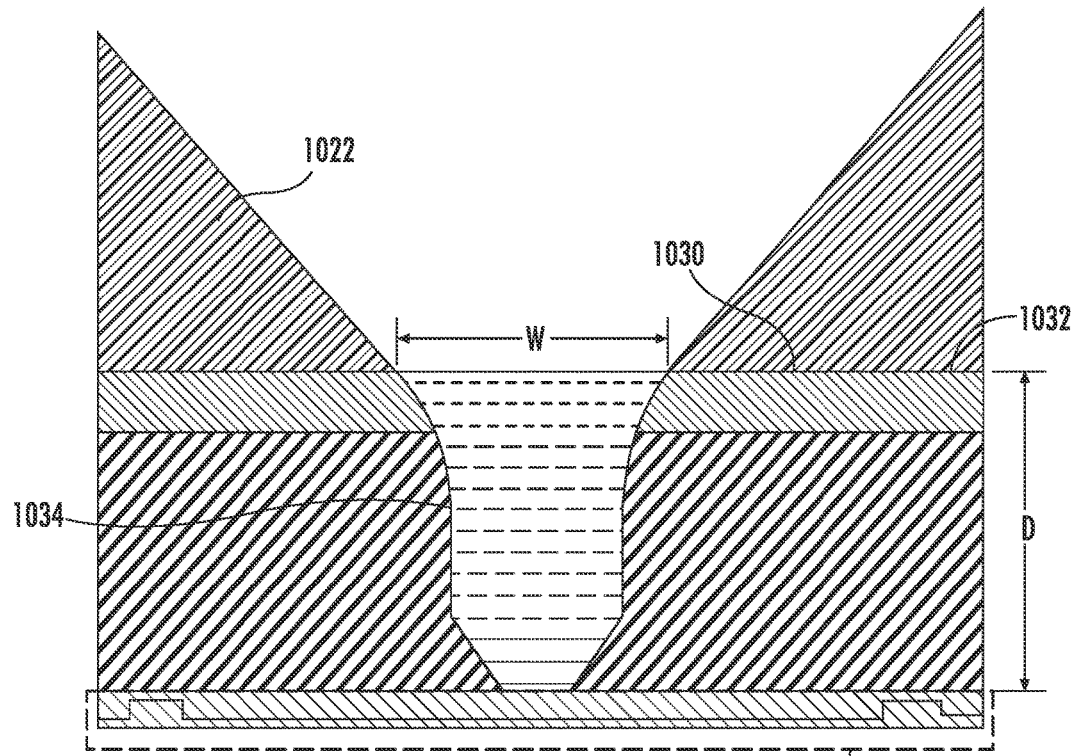
FIG. 11 is a fragmentary sectional view of a portion of the cassette board of FIG. 10A.

FIGS. 10A, 10B and 11 illustrate microfluidic chip 1030. FIG. 10A illustrates a top side of cassette board 1012, chip funnel 1022 and microfluidic chip 1030. FIG. 10A illustrates microfluidic chip 1030 sandwiched between chip funnel 1022 and cassette board 1012. FIG. 10B illustrate a bottom side of the set board 1012 and microfluidic chip 1030. FIG. 11 is a cross-sectional view of microfluidic chip 1030 below chip funnel 1022. As shown by FIG. 11, microfluidic chip 1030 comprises a substrate 1032 formed from a material such as silicon. Microfluidic chip 1030 comprises a microfluidic reservoir 1034 formed in substrate 1032 and which extends below chip funnel 1022 to receive the fluid sample (with a reagent in some tests) into chip 1030. In the example illustrated, microfluidic reservoir has a mouth or top opening having a width W of less than 1 mm and nominally 0.5 mm. Reservoir 1030 has a depth D of between 0.5 mm and 1 mm and nominally 0.7 mm. As will be described hereafter, microfluidic chip 1030 comprises pumps and sensors along a bottom portion of chip 1030 in region 1033.

Figure 12:
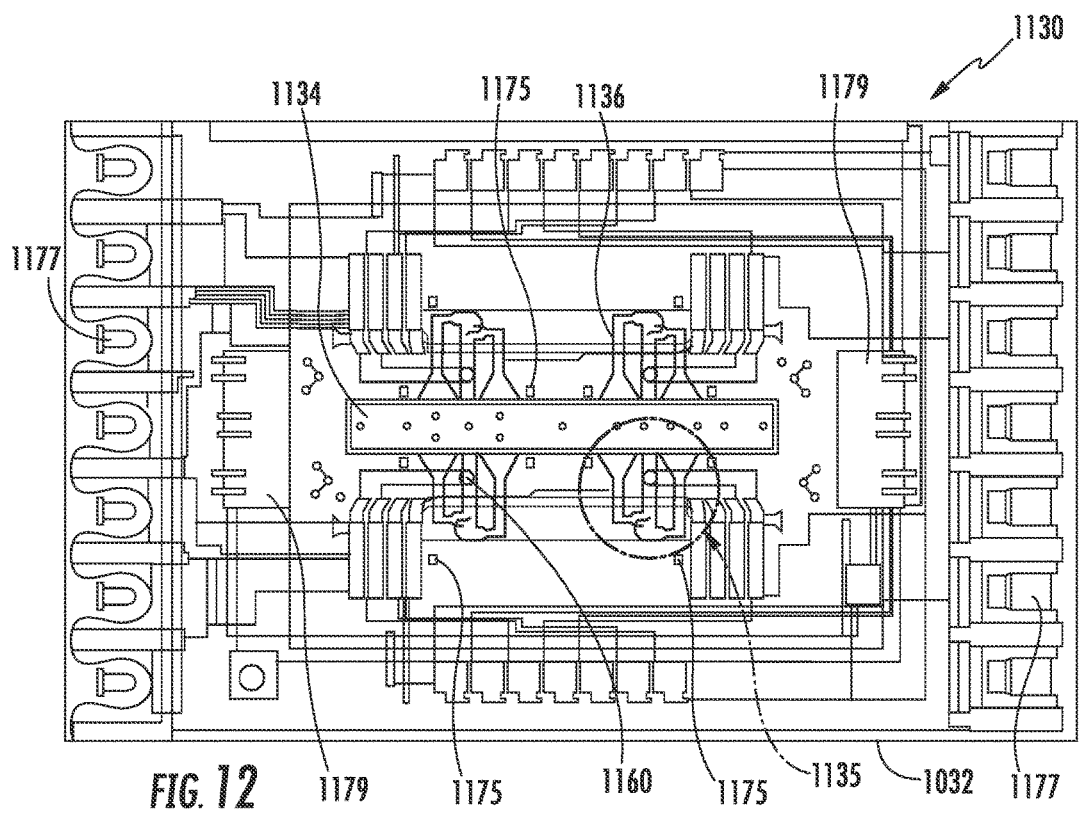
FIG. 12 is a top view of another example of the microfluidic chip of the cassette of FIGS. 8 and 9A.
Figure 13:
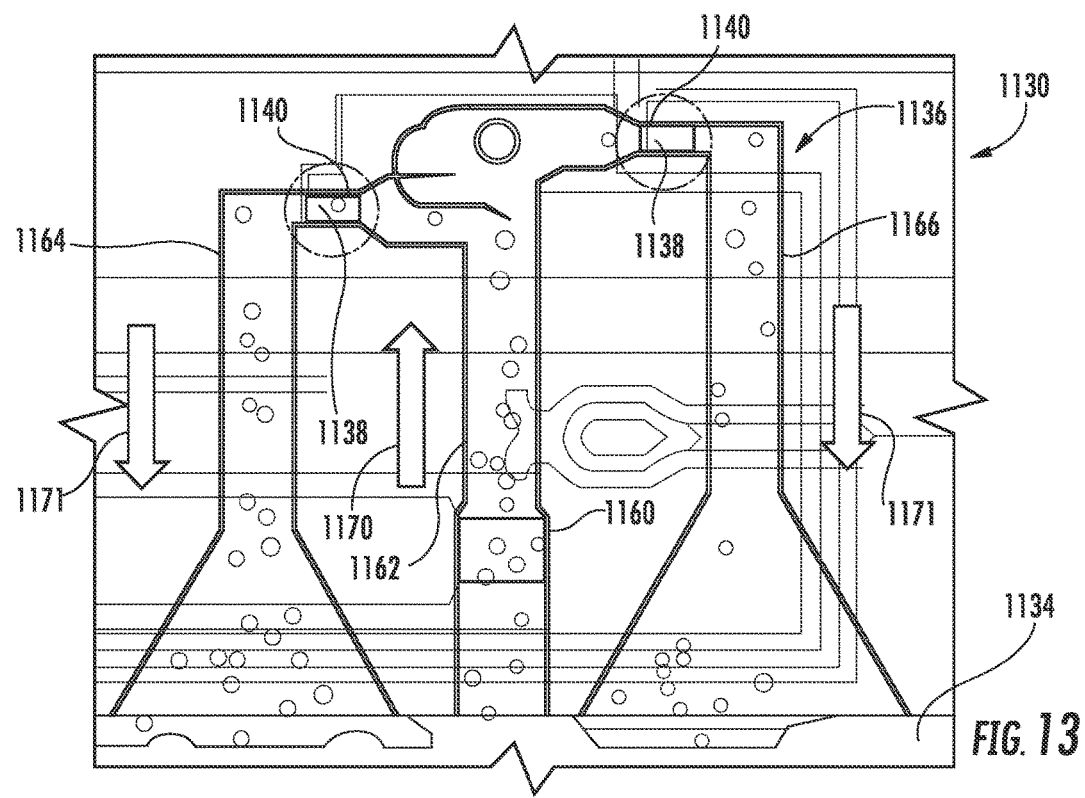
FIG. 13 is an enlarged fragmentary top view of an example sensing region of the microfluidic chip of FIG. 12.

FIGS. 12 and 13 are enlarged views of microfluidic chip 1130, an example implementation of microfluidic chip 1030. Microfluidic chip 1130 integrates each of the functions of fluid pumping, impedance sensing and temperature sensing on a low-power platform. Microfluidic chip 1130 is specifically designed for use with a cassette 1010 having a cassette body 1014 that omits discharge reservoir 1024. As will be described hereafter, microfluidic chip 1133 recirculates portions of a fluid sample, that has been tested, back to an input or upstream side of the sensors of microfluidic chip 1133. As shown by FIG. 12, microfluidic chip 1030 comprises substrate 1032 in which is formed microfluidic reservoir 1034 (described above). In addition, microfluidic chip 1130 comprises multiple sensing regions 735, each sensing region comprising a microfluidic channel 1136, micro-fabricated integrated sensors 1138, and a pump 1160.

FIG. 13 is an enlarged view illustrating one of sensing regions 1135 of chip 1130 shown in FIG. 12. As shown by FIG. 13, microfluidic channel 1136 comprises a passage extending within or formed within substrate 1032 for the flow of a fluid sample. Channel 1136 comprises a pump containing central portion 1162 and a pair of sensor containing branch portions 1164, 1166. Each of branch portions 1164, 1166 comprises a funnel-shaped mouth that widens towards microfluidic reservoir 1134. Central portion 1162 extends from reservoir 1134 with a narrower mouth opening to reservoir 1134. Central portion 1162 contains pump 1160.

Sensor containing branch portions 1164, 1166 stem or branch off of opposite sides of central portion 162 and extend back to reservoir 1134. Each of branch portions 1164, 1166 comprises a narrowing portion, throat or constriction 1140 through with the fluid flows. For purposes of this disclosure, a "constriction" means any narrowing in at least one dimension. A "constriction" may be formed by (A) one side of a channel having a protruberance projecting towards the other side of the channel, (B) both sides of a channel having at least one protruberance projecting towards the other side of the channel, wherein such multiple protruberances are either aligned with one another or are staggered along the channel or (C) at least one column or pillar projecting between two walls of the channel to discriminate against what can or cannot flow through the channel.

In one implementation, branch portions 1164, 1166 are similar to one another. In another implementation, branch portions 1164, 1166 are shaped or dimensioned different from one another so as to facilitate different fluid flow characteristics. For example, the constrictions 1140 or other regions of portions 1164, 1166 may be differently sized such that particles or cells of a first size more readily flow through, if at all, through one of portions 364, 366 as compared to the other of portions 1164, 1166. Because portions 1164, 1166 diverge from opposite sides of central portion 1162, both of portions 1164, 1166 receive fluid directly from portion 1162 without fluid being siphoned to any other portions beforehand.

Each of micro-fabricated integrated sensors 1138 comprises a micro-fabricated device formed upon substrate 1032 within constriction 1140. In one implementation, sensor 1138 comprises a micro-device that is designed to output electrical signals or cause changes in electrical signals that indicate properties, parameters or characteristics of the fluid and/or cells/particles of the fluid passing through constriction 1140. In one implementation, each of sensors 1138 comprises a cell/particle sensor that detects properties of cells or particles contained in a fluid and/or that detects the number of cells or particles in fluid passing across sensor 1138. For example, in one implementation, sensor 1138 comprises an electric sensor which outputs signals based upon changes in electrical impedance brought about by differently sized particles or cells flowing through constriction 1140 and impacting impedance of the electrical field across or within constriction 1140. In one implementation, sensor 1138 comprises an electrically charged high side electrode and a low side electrode formed within or integrated within a surface of channel 1136 within constriction 40. In one implementation, the low side electrode is electrically grounded. In another implementation, low side electrode comprises a floating low side electrode. For purposes of this disclosure, a "floating" low side electrode refers to an electrode having all connecting admittances zero. In other words, the floating electrode is disconnected, not being connected to another circuit or to earth.

Figure 14:
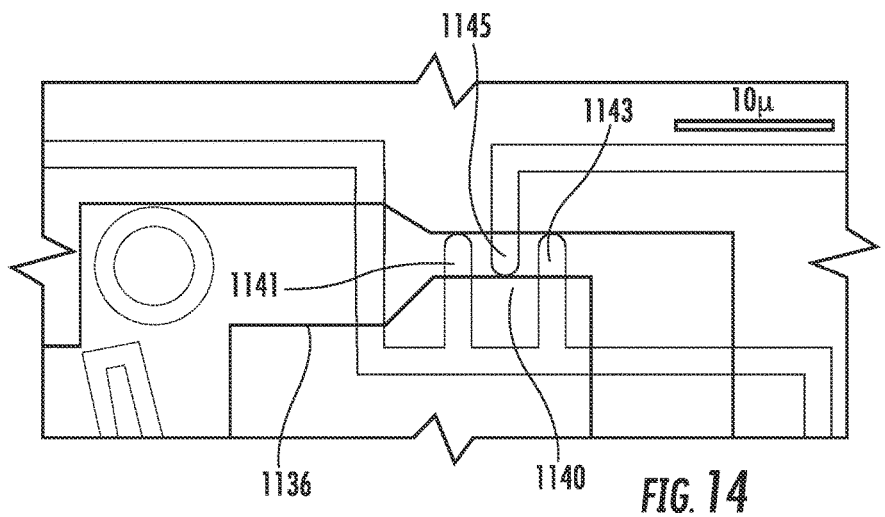
FIG. 14 is a fragmentary top view of an example microfluidic chip, illustrating an example electric sensor within an example microfluidic channel.
Figure 15:
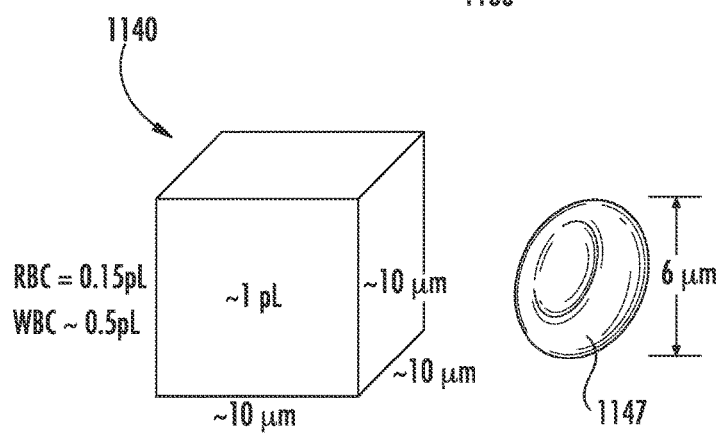
FIG. 15 is a diagram illustrating a volume of an example constriction of a microfluidic channel relative to an example cell.
Figure 16:
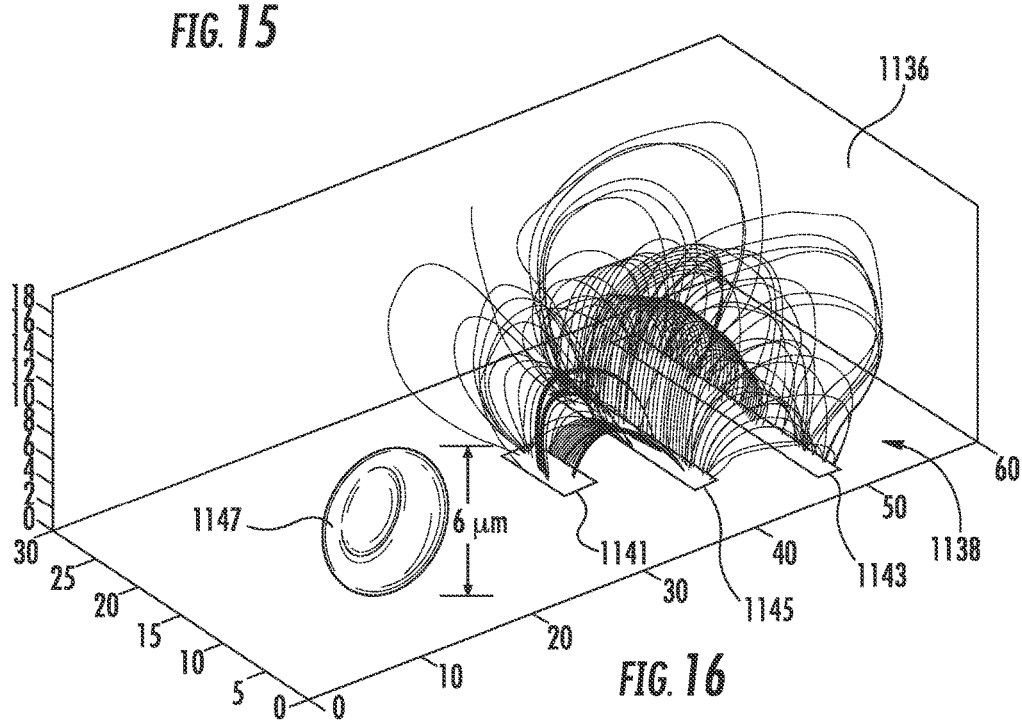
FIG. 16 is a diagram of an example microfluidic channel comprising an example electric sensor, illustrating the creation of an electric field and the relative size of the cell about to pass through the electric field.

FIGS. 14-16 illustrate one example of sensor 1138. As shown by FIG. 14, in one implementation, sensor 1138 comprises an electric sensor comprising low side electrodes 1141, 1143 and charged or active high side electrode 1145. Low side electrodes are either grounded or are floating. Active electrode 1145 is sandwiched between grounding electrodes 143. Electrodes 1141, 1143 and 1145, forming electric sensor 1138, are located within a constriction 1140 formed within channel 1136. Constriction 1140 comprises a region of channel 1136 that has a smaller cross-sectional area than both adjacent regions of channel 36, upstream and downstream of constriction 1140.

FIG. 15 illustrates one example sizing or dimensioning of constriction 1140. Constriction 1140 has a cross-sectional area similar to that of the individual particles or cells that pass through constriction 1140 and which are being tested. In one implementation in which the cells 1147 being tested have a general or average maximum dimension of 6 µm, constriction 1140 has a cross-sectional area of 100 µm². In one implementation, constriction 1140 has a sensing volume of 1000 µm³. For example, in one implementation, constriction 1140 has a sense volume forming a region having a length of 10 µm, a width of 10 µm and a height of 10 µm. In one implementation, constriction 1140 has a width of no greater than 30 µm. The sizing or dimensioning of constriction 1140 restricts the number of particles or individual cells that may pass through constriction 1140 at any one moment, facilitating testing of individual cells or particles passing through constriction 1140.

FIG. 16 illustrates the forming an electric field by the electrodes of electric sensor 1138. As shown by FIG. 16, low side electrodes 1143 share active or high side electrode 1145, wherein an electrical field is formed between active high side electrode 1145 and each of the two low side electrodes 1141, 1143. In one implementation, low side electrodes 1141, 1143 are likely grounded. In another implementation, low side electrode 1141, 1143 comprise floating low side electrodes. As fluid flows across the electrodes 1141, 1143, 1145 and through the electrical field, the particles, cells or other analyte within the fluid impact the impedance of the electrical field. This impedance is sensed to identify characteristics of the cells or particles or to count the number of cells or particles passing through the electric field.

Pump 1160 comprises a device to move fluid through microfluidic channel 1136 and through constrictions 1140 across one of sensors 1138. Pump 1160 draws fluid from microfluidic reservoir 1134 into channel 1136. Pump 1160 further circulates fluid that has passed through constriction 1140 and across sensor 1138 back to reservoir 1134.

In the example illustrated, pump 1160 comprises a resistor actuatable to either of a pumping state or a temperature regulating state. Resistor 60 is formed from electrically resistive materials that are capable of emitting a sufficient amount of heat so as to heat adjacent fluid to a temperature above a nucleation energy of the fluid. Resistor 1160 is further capable of emitting lower quantities of heat so as to heat fluid adjacent resistor 1160 to a temperature below a nucleation energy of the fluid such that the fluid is heated to a higher temperature without being vaporized.

When the resistor forming pump 1160 is in the pumping state, pulses of electrical current passing through the resistor cause resistor to produce heat, heating adjacent fluid to a temperature above a nucleation energy of the adjacent fluid to create a vapor bubble which forcefully expels fluid across constrictions 1140 and back into reservoir 34. Upon collapse of the bubble, negative pressure draws fluid from microfluidic reservoir 1134 into channel 1136 to occupy the prior volume of the collapsed bubble.

When the resistor forming pump 1160 is in the temperature regulating state or fluid heating state, the temperature of adjacent fluid rises to a first temperature below a nucleation energy of the fluid and then maintains or adjusts the operational state such that the temperature of the adjacent fluid is maintained constant or constantly within a predefined range of temperatures that is below the nucleation energy. In contrast, when resistor 1160 is being actuated to a pumping state, resistor 1160 is in an operational state such that the temperature of fluid adjacent the resistor 1160 is not maintained at a constant temperature or constantly within a predefined range of temperatures (both rising and falling within the predefined range of temperatures), but rapidly and continuously increases or ramps up to a temperature above the nucleation energy of the fluid.

In yet other implementations, pump 1160 may comprise other pumping devices. For example, in other implementations, pump 1160 may comprise a piezo-resistive device that changes shape or vibrates in response to applied electrical current to move a diaphragm to thereby move adjacent fluid across constrictions 1140 and back to reservoir 1134. In yet other implementations, pump 1160 may comprise other microfluidic pumping devices in fluid communication with microfluidic channel 1136.

As indicated by arrows in FIG. 13, actuation of pump 1160 to the fluid pumping state moves the fluid sample through central portion 1162 in the direction indicated by arrow 1170. The fluid sample flows through constrictions 1140 and across sensors 1138, where the cells within the fluid sample impact the electric field (shown in FIG. 16) and wherein the impedance is measured or detected to identify a characteristic of such cells or particles and/or to count the number of cells flowing across the sensing volume of sensor 1138 during a particular interval of time. After passing through constrictions 1140, portions of the fluid sample continue to flow back to microfluidic reservoir 1134 as indicated by arrows 1171.

As further shown by FIG. 12, microfluidic chip 1130 additionally comprises temperature sensors 1175, electrical contact pads 1177 and multiplex or circuitry 11 79. Temperature sensors 1175 are located at various locations amongst the sensing regions 1135. Each of temperature sensors 1175 comprises a temperature sensing device to directly or indirectly output signals indicative of a temperature of portions of the fluid sample in the microfluidic channel 1136. In the example illustrated, each of temperature sensors 1135 is located external to channel 36 to indirectly sense a temperature of the sample fluid within channel 1136. In other implementations, temperature sensors 1175 are located within microfluidic reservoir 1134 to directly sense a temperature of the sample fluid within reservoir 1134. In yet another implementation, temperature sensors 1175 are located within channel 1136. In yet other implementations, temperature sensor 240 may be located at other locations, wherein the temperature at such other locations is correlated to the temperature of the sample fluid being tested. In one implementation, temperature sensors 1135 output signals which are aggregated and statistically analyzed as a group to identify statistical value for the temperature of the sample fluid being tested, such as an average temperature of the sample fluid being tested. In one implementation, chip 1130 comprises multiple temperature sensors 1175 within reservoir 1134, multiple temperature sensors 1175 within channel 1136 and/or multiple temperature sensors external to the fluid receiving volume provided by reservoir 1134 and channel 1136, within the substrate of chip 1130.

In one implementation, each of temperature sensors 1175 comprises an electrical resistance temperature sensor, wherein the resistance of the sensor varies in response to changes in temperature such that signals indicating the current electrical resistance of the sensor also indicate or correspond to a current temperature of the adjacent environment. In other implementations, sensors 1175 comprise other types of microfabricated or microscopic temperature sensing devices.

Electrical contact pads 1177 are located on end portions of microfluidic chip 1130 which are spaced from one another by less than 3 mm and nominally less than 2 mm, providing microfluidic chip 1130 with a compact length facilitates the compact size of cassette 1010. Electrical contact pads 1177 sandwich the microfluidic and sensing regions 1135 and are electrically connected to sensors 1138, pumps 1160 and temperature sensors 1175. Electrical contact pads 1177 are further electrically connected to the electrical connectors 1016 of cassette board 1012 (shown in FIGS. 9B, 9C 10A and 10B.

Multiplexer circuitry 1179 is electrically coupled between electrical contact pads 1177 and sensors 1138, pumps 1160 and temperature sensors 1175. Multiplexer circuitry 1179 facilitates control and/or communication with a number of sensors 1138, pumps 1160 and temperature sensors 1175 that is greater than the number of individual electrical contact pads 1177 on chip 430. For example, despite chip 1130 having a number n of contact pads, communication is available with a number of different independent components having a number greater than n. As a result, valuable space or real estate is conserved, facilitating a reduction in size of chip 1130 and cassette 1010 in which chip 1130 is utilized. In other implementations, multiplexer circuitry 1179 may be omitted.

Figure 17:
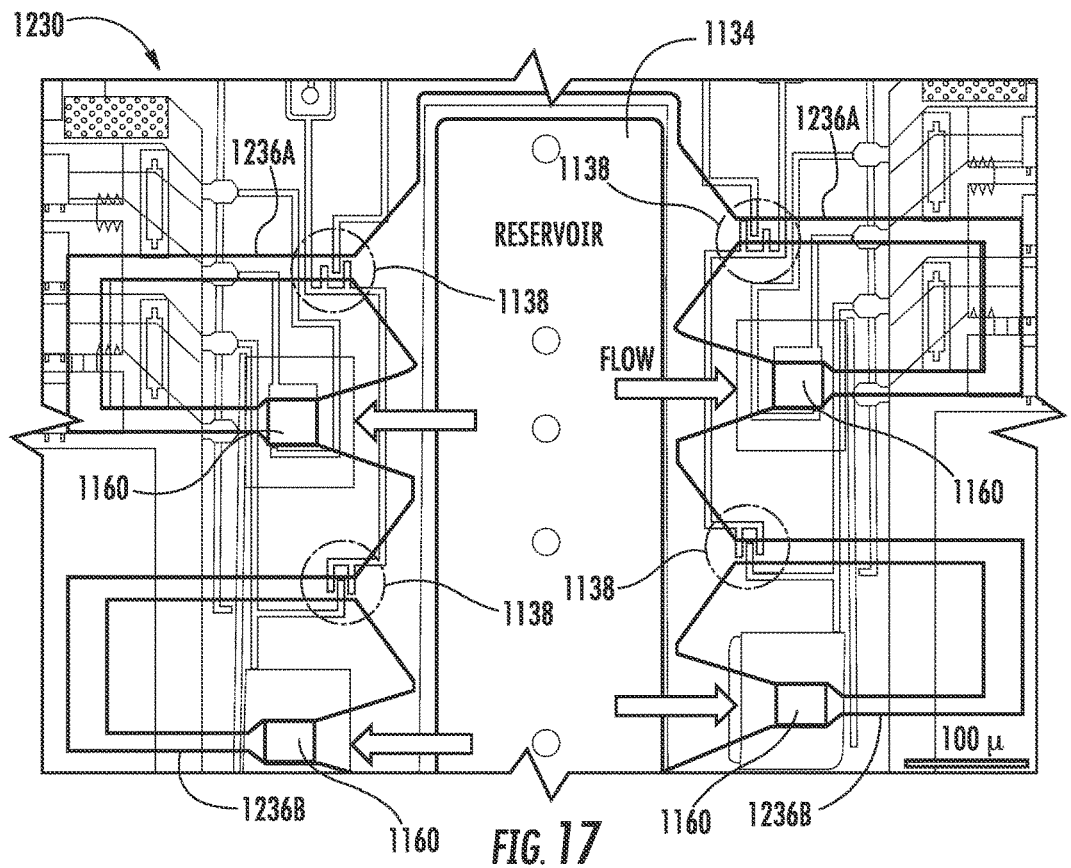
FIG. 17 is a fragmentary top view of another example microfluidic chip usable in the cassette of FIGS. 8 and 9A.

FIG. 17 is an enlarged view of a portion of microfluidic chip 1230, another example implementation of microfluidic chip 1030. Similar to microfluidic chip 1130, microfluidic chip 1430 comprises temperature sensors 1175, electrical contact pads 1177 and multiplexer circuitry 1179 illustrated and described above with respect to microfluidic chip 1130. Like microfluidic chip 1130, microfluidic chip 1230 comprises sensor regions comprising an electric sensor 1138 and a pump 1160. Microfluidic chip 1230 additionally comprises temperature sensors 1175 dispersed throughout. Microfluidic chip 1230 is similar to microfluidic chip 1130 except that microfluidic chip 1230 comprises differently sized or dimensioned microfluidic channels. In the example illustrated, microfluidic chip 1230 comprises U-shaped microfluidic channels 1236A and 1236B (collectively referred to as microfluidic channels 1236). Microfluidic channels 1236A have a first width while microfluidic channels 1236B have a second with less than the first width.

Because microfluidic channels 1236 have different widths or different cross-sectional areas, channels 12 36 receive differently sized cells or particles in the fluid sample for testing. In one such implementation, the different sensors 1138 in the differently sized channels 1236 are operated at different frequencies of alternating current such perform different tests upon the differently sized cells in the differently sized channels 1236. In another of such implementations, the differently sized channels 1236 contain a different type or differently designed electric sensor 1138 to detect different characteristics of the differently sized cells, particles or other analyte passing through the differently sized channels 1236.

Figure 18:
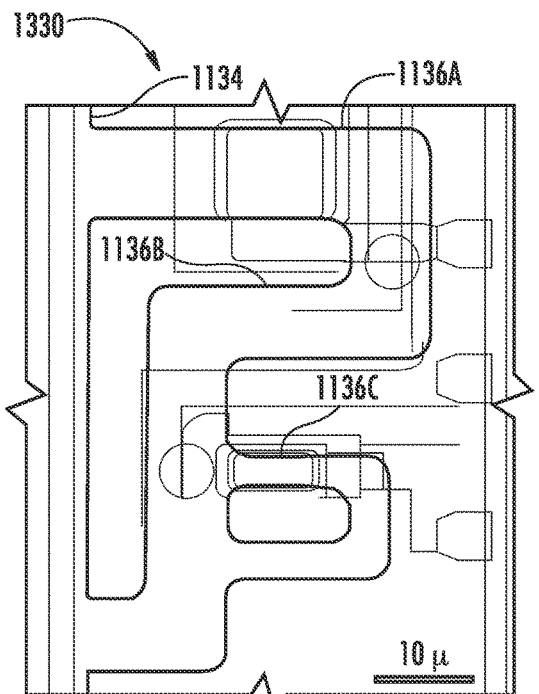
FIG. 18 is a fragmentary top view of another example microfluidic chip usable in the cassette of FIGS. 8 and 9A, illustrating example microfluidic channel portions.
Figure 19:
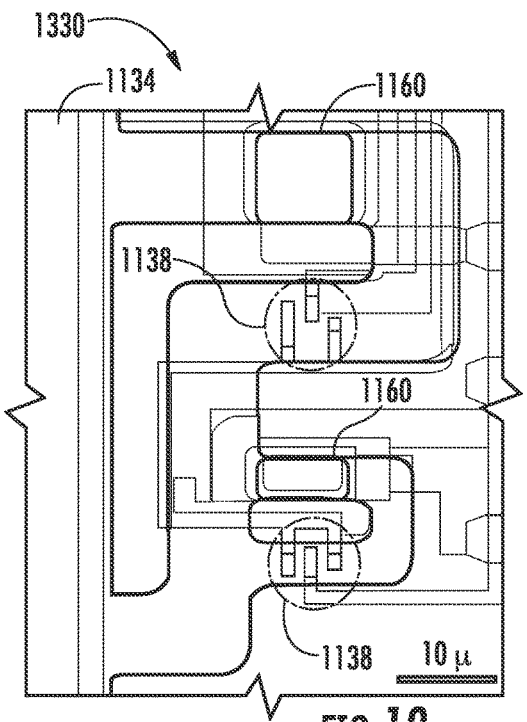
FIG. 19 is a fragmentary top view of the microfluidic chip of FIG. 18 illustrating example pumps and sensors within the microfluidic channel portions.

FIGS. 18 and 19 are enlarged views illustrating a portion of microfluidic chip 1330, another example implementation of microfluidic chip 1030. Similar to microfluidic chip 1130, microfluidic chip 1430 comprises temperature sensors 1175, electrical contact pads 1177 and multiplexer circuitry 1179 illustrated and described above with respect to microfluidic chip 1130. Microfluidic chip 1330 is similar to microfluidic chip 1230 in that microfluidic chip 1330 comprises microfluidic channel portions 1336A, 1336B and 1336C (collectively referred to as channels 1336) of varying widths. Microfluidic chip 1330 has a different geometry as compared to microfluidic chip 1230. As with microfluidic chip 1230, microfluidic chip 1330 comprises various sensing regions with the sensing region including an electric sensor 1138 and a pump 1160.

FIG. 18 omits sensors 1138 and pumps 1160 to better illustrate channels 1336. As shown by FIG. 18, channel portion 1336A has a width greater than the width of channel portion 1336B. Channel portion 1336B has a width greater than the width of channel portion 1336C. Channel portion 1336A extends from microfluidic reservoir 1134. Channel portion 1336B extends from channel portion 1336A and continues back to microfluidic reservoir 1134. Channel portion 1336C branches off of channel portion 1336B and returns to channel portion 1336B as shown by FIG. 19, pump 1160 is located within channel portion 1336A. Sensors 1138 are located within channel portion 1336B and channel portion 1336C. As a result, a single pump 1160 pumps a fluid sample through both of channel portions 1336B and 1336C across the respective sensors 1138 contained within the differently sized channels. Cells in all of the pumped fluid pass across and are sensed by sensor 1138 in channel portion 1336B. Those cells that are sufficiently small to pass through the narrower channel portion 1336C pass through and are sensed by the sensor 1138 in channel portion 1336C. As a result, the sensor 1138 and channel portion 1336C senses a subset or less than complete portion of the cells and fluid pumped by pump 1160.

Figure 20:
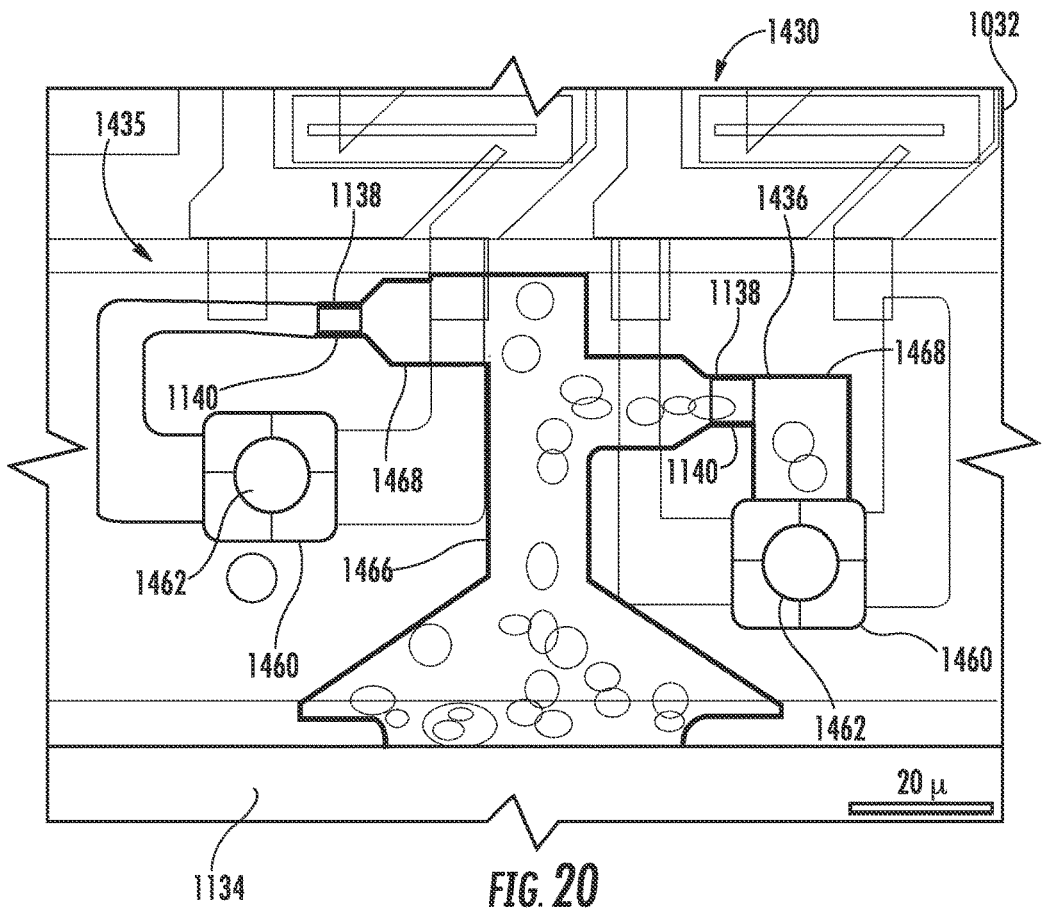
FIG. 20 is a fragmentary top view of another example microfluidic chip usable in the cassette of FIGS. 8 and 9A.

FIG. 20 is an enlarged view of a portion of microfluidic chip 1430, another example implementation of microfluidic chip 1030. Microfluidic chip 1430 is specifically designed for use with a cassette, such as cassette 1010, that comprises a discharge reservoir, such as discharge reservoir 1024 shown in FIG. 9A. Similar to microfluidic chip 1130, microfluidic chip 1430 comprises temperature sensors 1175, electrical contact pads 1177 and multiplexer circuitry 1179 illustrated and described above with respect to microfluidic chip 1130.

FIG. 20 illustrates one example sensing region 1435 of microfluidic chip 1430, wherein microfluidic chip 1430 comprises multiple such sensing regions 1435. Microfluidic sensing region 1435 comprises microfluidic channel 1436, fluid sensors 1138, pumps 1460 and discharge passages 1462. Microfluidic channel 1436 is formed in substrate 1032 and comprises inlet portion 1466 and branch portions 1468. Inlet portion 1466 has a funnel shaped mouth extending from microfluidic reservoir 1134. Inlet portion 466 facilitates inflow of fluid, including cells or particles, into channel 1436 and through each of branch portions 1468.

Branch portions 1468 extend from opposite sides of central portion 1466. Each of branch portions 1468 terminate at an associated discharge passage 1462. In the example illustrated, each of branch portions 1468 comprises a constriction 1140 in which the sensor 1138 is located.

Pumps 1460 are located proximate to and nominally opposite to discharge passages 1462 so as to pump fluid through discharge passages 1462 to the underlying discharge reservoir 1024 (shown in FIG. 9A). Pumps 1460 comprise resistors similar to pumps 1160 described above. In the pumping state, pumps 1460 receive electrical current the heat adjacent fluid to a temperature above a nucleation energy of the fluid so as to create a vapor bubble which pushes fluid between pump 1460 and discharge passage 1462 through discharge passage 1462 into the discharge reservoir 1024. Collapse of the vapor bubble draws portions of a fluid sample from microfluidic reservoir 1134, through central portion 1466 and across sensors 1138 in branch portions 1468.

Discharge passages 1462 extend from a portion of passage 1436 adjacent to pump 460 to discharge reservoir 156. Discharge passages 1462 inhibit reverse or backflow of fluid within discharge reservoir 1024 through discharge passages 1462 back into channel 1436. In one implementation, each of discharge passages 1462 comprises a nozzle through which fluid is pumped by pump 1460 into discharge reservoir 1024. In another implementation, discharge passage 1462 comprises a unidirectional valve.

Referring back to FIG. 7, cassette interface 1200 sometimes referred to as a "reader" or "dongle", interconnects and serves as an interface between cassette 1010 and mobile analyzer 1232. Cassette interface 1200 contains components or circuitry that is dedicated, customized or specifically adapted for controlling components of microfluidic cassette 1010. Cassette interface 1200 facilitates use of a general portable electronic device, loaded with the appropriate computer readable instructions and application program interface, but wherein the portable electronic device may omit the hardware or firmware specifically used to enable control of the components of cassette 1010. As a result, cassette interface 220 facilitates use of multiple different portable electronic devices 1232 which have simply been updated with an upload of an application program and an application programming interface. Cassette interface 1200 facilitates use of mobile analyzer 1232 that are not specifically designated or customized for use just with the particular microfluidic cassette 1010. Said another way, cassette interface 1200 facilitates use of mobile analyzer 1232 with multiple different cassettes 1010 having different testing capabilities through the connection of a different cassette interface 1200.

Cassette interface 220 carries circuitry and electronic components dedicated or customized for the specific use of controlling the electronic components of cassette 1010. Because cassette interface 1200 carries much of the electronic circuitry and components specifically dedicated for controlling the electronic components of cassette 1010 rather than such electronic components being carried by cassette 1010 itself, cassette 1010 may be manufactured with fewer electronic components, allowing the costs, complexity and size of cassette 1010 to be reduced. As a result, cassette 1010 is more readily disposable after use due to its lower base cost. Likewise, because cassette interface 1200 is releasably connected to cassette 210, cassette interface 1200 is reusable with multiple exchanged cassettes 1010. The electronic components carried by cassette interface 1200 and dedicated or customized to the specific use of controlling the electronic components of a particular cassette 1010 are reusable with each of the different cassettes 1010 when performing fluid or blood tests on different fluid samples or fluid samples from different patients or sample donors.

In the example illustrated, cassette interface 1200 comprises electrical connector 1204, electrical connector 1206 and firmware 1208 (schematically illustrated external to the outer housing of interface 1200). Electrical connector 1204 comprises a device by which cassette interface 1200 is releasably electrically connected directly to electrical connectors 1016 of cassette 1010. In one implementation, the electrical connection provided by electrical connector 1204 facilitates transmission of electrical power for powering electronic components of microfluidic chip 1030, 1130, 1230, 1330, 1430, such as electric sensors 1138 or a microfluidic pump 1160. In one implementation, the electrical connection provided by electrical connector 1204 facilitates transmission of electrical power in the form of electrical signals providing data transmission to microfluidic chip 1030, 1130, 1230, 1330, 1430 to facilitate control of components of microfluidic chip 1030, 1130, 1230, 1330, 1430. In one implementation, the electrical connection provided by electrical connector 1204 facilitates transmission of electrical power in the form electrical signals to facilitate the transmission of data from microfluidic chip 1030, 1130, 1230, 1330, 1430 to the mobile analyzer 1232, such as the transmission of signals from sensor sensors 38. In one implementation, electrical connector 1204 facilitates each of the powering of microfluidic chip 1030, 1130, 1230, 1330, 1430 as well as the transmission of data signals to and from microfluidic chip 1030, 1130, 1230, 1330, 1430.

In the example illustrated, electrical connectors 1204 comprise a plurality of electrical contact pads located in a female port, wherein the electrical contact pads which make contact with corresponding pads 1016 of cassette 1010. In yet another implementation, electrical connectors 1204 comprise a plurality of electrical prongs or pins, a plurality of electrical pin or prong receptacles, or a combination of both. In one implementation, electrical connector 1204 comprises a universal serial bus (USB) connector port to receive one end of a USB connector cord, wherein the other end of the USB connector cord is connected to cassette 210. In still other implementations, electrical connector 1204 may be omitted, where cassette interface 1200 comprises a wireless communication device, such as infrared, RF, Bluetooth other wireless technologies for wirelessly communicating between interface 1200 and cassette 1010.

Electrical connector 1204 facilitates releasable electrical connection of cassette interface 1200 to cassette 1010 such that cassette interface 1200 may be separated from cassette thousand 10, facilitating use of cassette interface 1200 with multiple interchangeable cassettes 1010 as well as disposal or storage of the microfluidic cassette 1010 with the analyzed fluid, such as blood. Electrical connectors 1204 facilitate modularization, allowing cassette interface 1200 and associated circuitry to be repeatedly reused while cassette 1010 is separated for storage or disposal.

Electrical connector 1206 facilitates releasable connection of cassette interface 1200 to mobile analyzer 1232. As a result, electrical connector 1206 facilitates use of cassette interface 1200 with multiple different portable electronic devices 1232. In the example illustrated, electrical connector 1206 comprises a universal serial bus (USB) connector port to receive one end of a USB connector cord 1209, wherein the other end of the USB connector cord 1209 is connected to the mobile analyzer 1232. In other implementations, electrical connector 1206 comprises a plurality of distinct electrical contact pads which make contact with corresponding blood connectors of mobile analyzer 1232, such as where one of interface 1200 and mobile analyzer 1232 directly plug into the other of interface 1200 and mobile analyzer 1232. In another implementation, electrical connector 1206 comprises prongs or prong receiving receptacles. In still other implementations, electrical connector 1206 may be omitted, where cassette interface 1200 comprises a wireless communication device, utilizing infrared, RF, Bluetooth or other wireless technologies for wirelessly communicating between interface 1200 and mobile analyzer 1232.

Firmware 1208 comprises electronic componentry and circuitry carried by cassette interface 1200 and specifically dedicated to the control of the electronic components and circuitry of microfluidic chip 1030, 1130, 1230, 1330, 1430 and cassette 1010. In the example illustrated, firmware 1208 serves as part of a controller to control electric sensors 1138.

As schematically shown by FIG. 7, firmware 1208 comprises at least one printed circuit board 1210 which supports frequency source 1212, and impedance extractor 1214 to receive first composite or base signals from the sensors 1138 and to extract impedance signals from the base signals and a buffer 1216 to store the impedance signals as or until the impedance signals are transmitted to mobile analyzer 1232. For example, in one implementation, impedance extractor 1214 performs analog quadrature amplitude modulation (QAM) which utilizes radiofrequency (RF) components to extract the frequency component out so that the actual shift in phase caused by impedance of the device under test (the particular sensor 1138) may be utilized.

Figure 21:
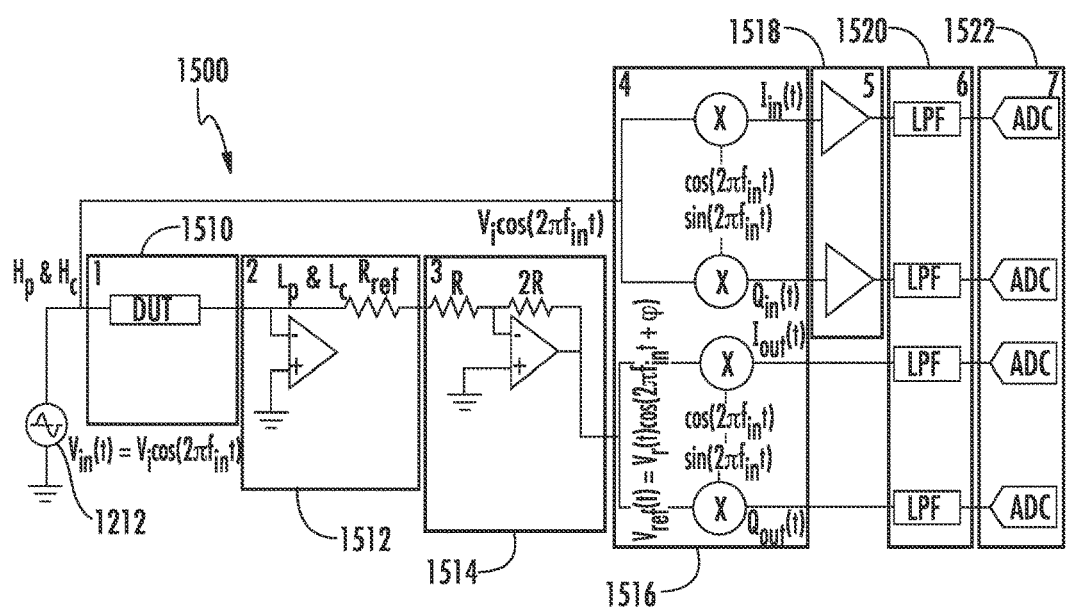
FIG. 21 is a schematic diagram of an example impedance sensing circuit.

FIG. 21 is a schematic diagram of an example impedance sensing circuit 1500 providing frequency source 1212 and impedance extractor 1214. In circuit block 1510, signals are measured from the high and low electrodes in the microfluidic channel 1136 (the device under test (DUT)). In circuit block 1512, the circuitry converts the current through the high low electrodes (device under test) to a voltage. In circuit block 1514, the circuitry conditions the voltage signals so as to have a correct phase and amplitude before and after the mixer, respectively. In circuit block 1516, the circuitry breaks the input and output voltage signals into real and imaginary parts. In circuit block 1518, the circuitry recovers each signal's amplitude. In circuit block 1520, the circuitry filters out high-frequency signals. In circuit block 1522, the circuitry converts the analog signals to digital signals where the digital signals are buffered by buffer 1216, such as with a field programmable gate array.

In one implementation, firmware 1208 comprises a field programmable gate array which serves as a frequency source controller and the buffer 1216. In another implementation, firmware 1208 comprises an application-specific integrated circuit (ASIC) serving as a frequency source controller, the impedance extractor 1214 and the buffer 1216. In each case, raw or base impedance signals from sensors 1138 are amplified and converted by an analog-to-digital converter prior to being used by either the field programmable gate array or the ASIC. In implementations where firmware 1208 comprises a field programmable gate array or an ASIC, the field programmable gate array or ASIC may additionally serve as a driver for other electronic components on microfluidic chip 1010 such as microfluidic pumps 1130 (such as resistors), temperature sensors 1175 and other electronic components upon the microfluidic chip.

Mobile analyzer 1232 comprises a mobile or portable electronic device to receive data from cassette 1010. Mobile analyzer 1232 is releasably or removably connected to cassette 1010 indirectly via cassette interface 1200. Mobile analyzer 1232 performs varies functions using data received from cassette 1010. For example, in one implementation, mobile analyzer 1232 stores the data. In the example illustrated, mobile analyzer 1232 additionally manipulates or processes the data, displays the data and transmits the data across a local area network or wide area network (network 1500) to a remote analyzer 1300 providing additional storage and processing.

In the example illustrated, mobile analyzer 1232 comprises electrical connector 1502, power source 1504, display 1506, input 1508, processor 1510, and memory 1512. In the example illustrated, electrical connector 1502 is similar to electrical connectors 1206. In the example illustrated, electrical connector 1502 comprises a universal serial bus (USB) connector port to receive one end of a USB connector cord 1209, wherein the other end of the USB connector cord 1209 is connected to the cassette interface 1200. In other implementations, electrical connector 1502 comprises a plurality of distinct electrical contact pads which make contact with corresponding electrical connectors of interface 1200, such as where one of interface 1200 and mobile analyzer 1232 directly plug into the other of interface 1200 and mobile analyzer 1232. In another implementation, electrical connector 1206 comprises prongs or prong receiving receptacles. In still other implementations, electrical connector 1502 may be omitted, where mobile analyzer 1232 and cassette interface 1200 each comprise a wireless communication device, utilizing infrared, RF, Bluetooth or other wireless technologies for facilitating wireless communication between interface 1200 and mobile analyzer 1232.

Power source 1504 comprise a source of electrical power carried by mobile analyzer 1232 for supplying power to cassette interface 1200 and cassette 1010. Power source 1504 comprises various power control electronic componentry which control characteristics of the power (voltage, current) being supplied to the various electronic components of cassette interface 1200 and cassette 1010. Because power for both cassette interface 1200 and cassette 1010 are supplied by mobile analyzer 1232, the size, cost and complexity of cassette interface 1200 and cassette 1010 are reduced. In other implementations, power for cassette 1010 and cassette interface 1200 are supplied by a battery located on cassette interface 1200. In yet another implementation, power for cassette 1010 is provided by a battery carried by cassette 1010 and power for interface 1200 is supplied by a separate dedicated battery for cassette interface 1200.

Display 1506 comprises a monitor or screen by which data is visually presented. In one implementation, display 1506 facilitates a presentation of graphical plots based upon data received from cassette 1010. In some implementations, display 1506 may be omitted or may be replaced with other data communication elements such as light emitting diodes, auditory devices are or other elements that indicate results based upon signals or data received from cassette 1010.

Input 1508 comprises a user interface by which a person may input commands, selection or data to mobile analyzer 1232. In the example illustrated, input 1508 comprise a touch screen provided on display 1506. In one implementation, input 1508 may additionally or alternatively utilize other input devices including, but are not limited to, a keyboard, toggle switch, push button, slider bar, a touchpad, a mouse, a microphone with associated speech recognition program and the like. In one implementation, input 1506 facilitates input of different fluid tests or modes of a particular fluid test pursuant to prompts provided by an application program run on mobile analyzer 1232.

Processor 1510 comprises at least one processing unit designed to generate control signals controlling the operation of sensors 1138 as well as the acquisition of data from sensors 1138. Processor 1510 further outputs control signals controlling the operation of pumps 1160 and temperature sensors 1175. In the example illustrated, processor 572 further analyzes data received from chip 230 to generate output that is stored in memory 1512, displayed on display 1506 and/or further transmitted across network 1500 to remote analyzer 1300.

Memory 1512 comprises a non-transitory computer-readable medium containing instructions for directing the operation of processor 1510. As schematically shown by FIG. 7, memory 1512 comprises or stores an application programming interface 1520 and application program 1522. Application programming interface 1520 comprises a library of routines, protocols and tools, which serve as building blocks, for carrying out various functions or tests using cassette 1010. Application programming interface 1520 comprises programmed logic or machine-readable instructions that accesses the library and assembles the "building blocks" or modules to perform a selected one of various functions or tests using cassette 1010. For example, in one implementation, application programming interface 1520 comprises an application programming interface library that contains routines for directing the firmware 1208 to place electric sensors 1138 in selected operational states, such as through the application of different frequencies of alternating current. In the example illustrated, the library also contains routines for directing firmware 1208 to operate fluid pumps 1160 or dynamically adjusts operation of such pumps 1160 or electric sensors 1138 in response to a sensed temperature of the fluid being tested from temperature sensors 1175. In one implementation, mobile analyzer 1232 comprises a plurality of application programming interfaces 1520, each application programming interface 1520 being specifically designed are dedicated to a particular overall fluid or analyte test. For example, one application programming interface 1520 may be directed to performing cytology tests. Another application program interface 1520 may be directed to performing coagulation tests. In such implementations, the multiple application programming interfaces 1520 may share the library of routines, protocols and tools.

Application programming interface 1520 facilitates testing of fluids using cassette 1010 under the direction of different application programs. In other words, application programming interface 1520 provides a universal programming set of commands for firmware 1208 that may be used by any of a variety of different application programs. For example, a user of mobile analyzer 1232 is able to download or install any of a number of different application programs, wherein each of the different application programs is designed to utilize the application program interface 1520 so as to carry out tests using cassette 1010. As noted above, firmware 1208 interfaces between application programming interface 1520 and the actual hardware or electronic componentry found on the cassette 1010 and, in particular, microfluidic chip 1030, 1130, 1230, 1330, 1430.

Application program 1522 comprises an overarching program contained in memory 1512 that facilitates user interaction with application programming interface 1520 or the multiple application programming interfaces 1520 stored in memory 1512. Application program 1522 presents output on display 1506 and receives input through input 1508. Application program 1522 communicates with application program interface 1520 in response to input received through input 1508. For example, in one implementation, a particular application program 1522 presents graphical user interfaces on display 1506 prompting a user to select which of a variety of different testing options are to be run using cassette 1010. Based upon the selection, application program 1522 interacts with a selected one of the application programming interfaces 1520 to direct firmware 1208 to carry out the selected testing operation using the electronic componentry of cassette 1010. Sensed values received from cassette 1010 using the selected testing operation are received by firmware 1208 and are processed by the selected application program interface 1520. The output of the application programming interface 1520 is generic data, data that is formatted so as to be usable by any of a variety of different application programs. Application program 1522 presents the base generic data and/or performs additional manipulation or processing of the base data to present final output to the user on display 1506.

Although application programming interface 1520 is illustrated as being stored in memory 1512 along with the application program 1522, in some implementations, application programming interface 1520 is stored on a remote server or a remote computing device, wherein the application program 1522 on the mobile analyzer 1232 accesses the remote application programming interface 1520 across a local area network or a wide area network (network 1500). In some implementations, application programming interface 1520 is stored locally on memory 1512 while application program 1522 is remotely stored a remote server, such as server 1300, and accessed across a local area network or wide area network, such as network 1500. In still other implementations, both application programming interface 1520 and application program 1522 are contained on a remote server or remote computing device and accessed across a local area network or wide area network (sometimes referred to as cloud computing).

In the example illustrated, system 1000 facilitates a reduction in size o chip 1130 by utilizing multiplexer circuitry with the provision of multiplexer circuitry 1179 and associated multiplexer circuitry on interface 1200 or mobile analyzer 1232. System 1000 further facilitates the reduction in size a chip 1130 through the appropriate allocation of the total transmission bandwidth of chip 1130 amongst the different controlled devices of chip 1130, such as fluid sensors 1138, pumps 1140 and temperature sensors 1175. Transmission bandwidth comprises the total capacity for the transmission of signals across and between connectors of port 1204 and 1177. Processor 1510 allocates the total transmission bandwidth by controlling the timing and rate at which control signals are output and sent across connectors of port 1204 and connectors of 1177 to the various controlled devices fluid sensors 1138, pumps 1160 and temperature sensors 1175 as well the timing and rate at which controlled devices are polled for data signals or at which data is received from the controlled devices. Instead of equally apportioning such bandwidth amongst all the controlled devices 1138, 1160, 1175 or amongst the different types or classes of controlled devices such as fluid sensors, temperature sensors and pumps, processor 1510, following instructions contained in memory 1512, differently allocates the transmission bandwidth amongst the different controlled devices.

The different allocation of the total transmission bandwidth across the controlled devices 1138, 1160, 1175 is based upon the class of controlled device or the generic function being performed by the different controlled devices. For example, in one implementation, a first portion of the total transmission bandwidth is allocated to sensors 1138, a second portion, different than the first portion, of the total transmission bandwidth is allocated to temperature sensors 1175 and a third portion of the total transmission bandwidth, different from the first portion and a second portion, is allocated to pumps 1160. In one implementation, the first portion of the total transmission bandwidth allocated to sensors 1138 is uniformly or equally apportioned amongst the different individual sensors 1138, the second portion of the total transmission bandwidth allocated to temperature sensors 1175 is uniformly or equally apportioned amongst the different individual temperature sensors 1175 and the third portion of the total transmission bandwidth allotted to pumps 1160 is uniformly or equally apportioned amongst different individual controlled devices 1160.

In another implementation, the first portion, the second portion and the third portion of the total transmission bandwidth are each non-uniformly or unequally apportioned amongst the individual controlled devices of each class 1138, 1175, 1160 of the controlled devices. In one implementation, different fluid sensors 1138 operate differently, to form different tests upon a fluid sample. For example, in one implementation in which sensors 1138 comprise electric sensors, one of fluid sensors 1138 is provided with a first frequency of alternating current while another of the fluid sensors 1138 is provided with a second different frequency of alternating current such that the two sensors output signals that indicate different parameters are characteristics of the cells or particles being sensed. In such an implementation, processor 1510 allocates each of the different sensors with a different percentage or portion of the total transmission bandwidth based upon the different tests or based on the different frequencies of alternating current being applied to the different sensors.

In one implementation, the allocation or apportionment of the total transmission bandwidth amongst individual controlled devices is additionally based upon characteristics of the individual controlled device itself relative to other controlled devices in the same class devices. For example, in one implementation, different sensors 1138 are located within differently sized constrictions. Such differently sized constrictions may result in a different concentration of cells or particles in the fluid flowing across or through the constriction, a different frequency at which cells are particles flow through the constriction or a different fluid flow rate across the constriction, the geometry of the portion of the fluid channel 1136 in which the sensors 1138 are located. In one implementation, those sensors 1138 located within constrictions having a greater fluid flow rate or a greater frequency at which cells or particles flow across such sensors are allocated a greater percentage of the total transmission bandwidth apportioned to the class of sensors as compared to other of such sensors in the class that are located within constrictions having lower fluid flow rates or a lower frequency at which cells are particles flow across such sensors.

Likewise, in some implementations, different pumps 1160 are located in differently designed microfluidic channels 1136, different portions of a channel 1136 with different geometries. As a result, the fluid flow or pumping demands placed upon the different pumps 1160 may also differ. In such implementations, those particular pumps 1160 having greater pumping demands are allocated a greater percentage of the total transmission bandwidth apportioned to the class of pumps as compared to other of such pumps in the class that located within channels 1136 that have lesser pumping demands. For example, in one implementation, a pump which is to move fluid through a longer microfluidic channel or a more tortuous microfluidic channel is provided with a greater percentage of the total transmission bandwidth to allow more frequent pulses and more frequent pumping as compared to another pump which is to move fluid through a shorter microfluidic channel or less tortuous microfluidic channel.

In one implementation, processor 1510 allocates a total transmission bandwidth such that processor 1510 polls and receives data from each of the sensors 1138 at a frequency of at least once every 2 μs. In such an implementation, processor 1510 transmits pulses to pumps 1160, comprising resistors, at a frequency of at least once every 100 μs not more frequent than once every 50 μs. In such an implementation, processor 1510 polls and receives data signals from temperature sensors 1175 at a frequency of at least once every 10 ms and not more frequent than once every 1 ms. In yet other implementations, other total transmission bandwidth allocations are employed.

In one implementation, processor 1510 flexibly or dynamically adjust the bandwidth allocation amongst the different controlled devices 138 based upon signal quality/resolution. For example, if a first amount of bandwidth allocated to impedance sensing by sensor 1138 is insufficient because the cells or other analyte are moving past sensor 1138 too fast such that the signal quality/resolution fails to satisfy a predetermined stored signal quality/resolution threshold, processor 1510 may automatically or in response to suggesting a bandwidth allocation increase to the user and receiving authorization from the user, increase the bandwidth allocation to the particular sensor 1138. Conversely, if a particular sensor 1138 has a lower fluid or cell flow rate due to the pumping rate, such that the allocated bandwidth exceeds the amount for achieving satisfactory signal quality/resolution, processor 1510 automatically, or responses suggesting a bandwidth allocation decrease of the user and receiving authorization from the user, decrease the bandwidth allocation to the particular sensor, wherein processor 1510 allocates the now freed bandwidth to another one of sensors 1138.

In the example illustrated in which sensors 1138 comprise electric sensors, application program 1522 and application programming interface 1520 cooperate to direct processor 1510 to control the frequency of the alternating current being applied to each of the sensors 1138 on-chip 1130. With respect to each individual sensor 1138, processor 1510 is directed to apply different non-zero frequencies of alternating current to an individual sensor 1138. In one implementation, processor 1510 dynamically adjusts the frequency of alternating current being applied to electric sensor 1138 based upon real time are ongoing performance of electric sensor 1138 to improve system performance. For example, in one implementation, controller 1510 outputs control signals that apply a first non-zero frequency of alternating current to a selected electric sensor 1138. Based upon signals received from the selected electric sensor 1138 during the application of the first non-zero frequency of alternating current, controller 1510 adjusts the value of the subsequently applied frequency of alternating current applied to electric sensor 1138. Processor 1510 outputs control signals such that frequency source 1212 applies a second non-zero frequency of alternating current to the selected electric sensor 1138, wherein a value of the second non-zero frequency of alternating current applied by frequency source 1212 to the selected electric sensor 1138 is based upon signals received from the electric sensor 1138 during the application of the first non-zero frequency of alternating current.

In one implementation, processor 1510 selectively applies different non-zero frequencies of alternating current to perform different tests upon the fluid sample. As a result of processor 1510 causing frequency source 1212 to apply different non-zero frequencies of alternating current to the electric sensor 1138, the electric sensor 1138 performs different tests, outputting different signals that may indicate different properties or characteristics of the fluid, or cells contained therein. Such different tests are performed on a single fluid sample on a single fluid testing platform without the fluid sample having to be transferred from one testing device to another. As a result, integrity the fluid sample is maintained, the cost and complexity of performing the multiple different tests is reduced and the amount of potentially bio-hazardous waste is also reduced.

In one implementation, application program 1522 directs processor 1510 to prompt a user for selection of a particular fluid test to be carried out by system 1000. In one implementation, application program 1522 causes processor 1510 to display on display 1506, for selection by user, different names of different tests or the characteristics or cell/particle parameters for selection. For example, processor 1510 may display cell count, cell size or some other parameter for selection by the user using input 1508.

In one implementation, prior to prompting a user for selection of a particular fluid test, application program 1522 to direct processor 1510 to carry out a check with the fluid testing device providing electric sensor 1138 to determine or identify what fluid tests or what frequency ranges are available or for which the fluid testing device is capable of providing. In such an implementation, program 1522 automatically eliminates those fluid tests that cannot be provided by the particular cassette 1010 from the list or menu of possible choices of fluid tests being presented to the user. In yet another implementation, application program 1522 presents a full menu of fluid tests, but notifies the user of those particular fluid tests that are not presently available or selectable given the current cassette 1010 connected to analyzer 1232.

Based upon the received selection for the fluid test to be carried out, processor 1510, following instructions contained in application program 1522, selects a scan range of frequencies of alternating current which is to be crossed or covered during testing with the electric sensor 1138. The scan range is a range across which multiple different frequency of alternating current are to be applied to electric sensor 38 according to a predefined scan profile. The scan range identifies the endpoints for a series of different frequencies of alternating current to be applied to electric sensor 1138 during testing. In one implementation, a scan range of 1 kHz to 10 MHz is applied to a sensor 1138.

The scan profile indicates the specific AC frequency values between the endpoints of the range and their timing of their application to electric sensor 1138. For example, a scan profile may comprise a continuous uninterrupted series of AC frequency values between the endpoints of the scan range. Alternatively, a scan profile may comprise a series of intermittent AC frequency values between the endpoints of the scan range. The number, time interval spacing between different frequencies and/or the incrementing of the frequency values themselves may be uniform or non-uniform in different scan profiles.

In one implementation or user selected mode of operation, processor 1510 carries out the identified scan range and scan profile to identify a frequency that provides the greatest signal-to-noise ratio for the particular testing carried out. After a fluid sample is added and portions of the fluid sample have reached a sense zone and have been detected at the sense zone, the associate pump 1160 is deactivated such that the analyte (cell or particle) is static or stationary in the sense zone of the adjacent sensor 1138. At this time, processor 1510 carries out the scan. During the scan, the frequency of alternating current applied to the particular sensor 1138 which results in the greatest signal-to-noise ratio is identified by processor 1510. Thereafter, pump 1160 which pumps fluid across the particular sensor 1138 is once again activated and the fluid sample is tested using the sensor 1138 with the identified frequency of alternating current being applied to the sensor 1138. In another implementation, a predetermined nominal frequency of alternating current is identified based upon the particular fluid test being performed, wherein multiple frequencies around the nominal frequency are applied to sensor 1138.

In one implementation or user selected mode of operation, processor 1510 identifies the particular range most suited for the fluid test selected by the, wherein the scan profile is a default profile, being the same for each of the different ranges. In another implementation or user selected mode of operation, processor 1510 automatically identifies the particular scan range most suited for the selected fluid test, wherein the user is prompted to select a scan profile. In another implementation or user selected mode of operation, processor 1510, following instructions provided by application program 1522, automatically identifies not only the most appropriate range for the particular fluid test selected by the user, but also the particular scan profile for the particular range for the particular fluid test selected by the user. In still another implementation or user selectable mode of operation, the user is prompted to select a particular scan profile, wherein processor 1510 identifies the most appropriate scan range, given the selected scan profile for the particular selected fluid test. In one implementation, memory 1512, or a remote memory, such as memory 1604, contains a lookup table which identifies different scan ranges in different scan profiles for different available or selectable fluid tests or fluid/cell/particle parameters for which a fluid test may be performed.

One implementation in which sensors 1138 comprise electric sensors, application program interface 1520 and application program 1522 cooperate to direct processor 1510 to apply different frequencies of alternating current to different sensors 1138 on the same microfluidic chip 1130 of cassette 1010. In one implementation, processor 1510 provides user selection of the different non-zero frequencies of alternating current applied to the different electric sensors 38. Because processor 1510 directs frequency source 1512 applies different non-zero frequencies of alternating current to the different electric sensors 1138, the different electric sensors 1138 perform different tests, outputting different signals that may indicate different properties or characteristics of the fluid, or cells contained therein. Such different tests are performed on a single fluid sample on a single fluid testing platform without the fluid sample having to be transferred from one testing device to another. As a result, integrity the fluid sample is maintained, the cost and complexity of performing the multiple different tests is reduced and the amount of potentially biohazardous waste is also reduced.

In the example illustrated, application program 1522 and application programming interface 1520 further cooperate to direct processor 1510 to regulate the temperature of the fluid sample being tested by cassette 1010. Application program 1522, application programming interface 1520 and processor 1510 serve as a controller that facilitates the dual-purpose functioning of resistors serving as pumps 1160 to achieve both fluid pumping and fluid temperature regulation. In particular, processor 1510 actuates resistor to a fluid pumping state by outputting control signals causing a sufficient amount of electrical current to pass through pump 1160 such that resistor of pump 1160 heats adjacent fluid within a microfluidic channel 1136, 1236, 1336, 1436 to a temperature above a nucleation energy of the fluid. As a result, the adjacent fluid is vaporized, creating a vapor bubble having a volume larger than the volume of the fluid from which the vapor bubble was formed. This larger volume serves to push the remaining fluid that was not vaporized within the channel to move the fluid across sensor 1138 or the multiple senses 1138. Upon collapse of the vapor bubble, fluid is drawn from reservoir 1134 into the channel to occupy the previous volume of the collapsed paper bubble. Processor 1510 actuates the resistor of pump 1160 to the pumping state in an intermittent or periodic fashion. In one implementation, processor 1510 actuates the resistor of pump 1160 to the pumping state in a periodic fashion such that the fluid within the microfluidic channel is continuously moving or continuously circulating.

During those periods of time that the resistor of pump 1160 is not being actuated to the pumping state, to a temperature above the nucleation energy of the fluid, processor 1510 uses the same resistor of pump 1160 to regulate the temperature of the fluid for at least those periods the time that the fluid is extending adjacent to or opposite to sensor 1138 and is being sensed by sensor 1138. During those periods the time that resistor 1160 is not in the pumping state, processor 1510 selectively actuates the resistor of pump 1160 to a temperature regulation state in which adjacent fluid is heated without being vaporized. Processor 1510 actuates resistor of pump 1160 to a fluid heating or temperature regulating state by outputting control signals causing a sufficient amount of electrical current to pass through resistor of pump 1160 such that the resistor of pump 1160 heats adjacent fluid within the microfluidic channel to a temperature below a nucleation energy of the fluid, without vaporizing the adjacent fluid. For example, in one implementation, controller actuates resistor to an operational state such that the temperature of adjacent fluid rises to a first temperature below a nucleation energy of the fluid and then maintains or adjusts the operational state such that the temperature of the adjacent fluid is maintained constant or constantly within a predefined range of temperatures that is below the nucleation energy. In contrast, when the resistor of pump 1160 is being actuated to a pumping state, pump 1160 is in an operational state such that the temperature of fluid adjacent the resistor of pump 1160 is not maintained at a constant temperature or constantly within a predefined range of temperatures (both rising and falling within the predefined range of temperatures), but rapidly and continuously increases or ramps up to a temperature above the nucleation energy of the fluid.

In one implementation, processor 1510 controls the supply of electrical current across the resistor of pump 1160 such that the resistor operates in a binary manner when in the temperature regulating state (the temperature of the adjacent fluid is not heated to a temperature above its nucleation energy). In implementations where the resistor of pump 1160 operates in a binary manner in the temperature regulating state, the resistor of pump 1160 is either "on" or "off". When the resistor of pump 1160 is "on", a predetermined amount of electrical current is passed through the resistor of pump 1160 such the resistor of pump 1160 emits a predetermined amount of heat at a predetermined rate. When the resistor of pump 1160 is "off", electrical current is not passed through the resistor such that resistor does not generate or emit any additional heat. In such a binary temperature regulating mode of operation, processor 1510 controls the amount of heat applied to the fluid within my clinic channel by selectively switching the resistor of pump 1160 between the "on" and "off" states.

In another implementation, processor 1510 controls or sets the resistor of pump 1160 at one of a plurality of different "on" operational states when in the temperature regulation state. As a result, processor 1510 selectively varies the rate at which heat is generated and emitted by the resistor of pump 1160, the heat emitting rate being selected from amongst a plurality of different available non-zero heat emitting rates. For example, in one implementation, Processor 1510 selectively varies or controls a rate at which heat is amended by the resistor of pump 1160 by adjusting a characteristic of pump 1160. Examples of a characteristic of the resistor of pump 1160 (other than an on-off state) that may be adjusted include, but are not limited to, adjusting a non-zero pulse frequency, a voltage and a pulse width of electrical current supplied across the resistor. In one implementation, Processor 1510 selectively adjusts multiple different characteristics to control or regulate the rate at which heat is being emitted by the resistor of pump 1160.

In one user selectable operational mode, processor 1510, following instructions from application programming interface 1520 and application program 52, selectively actuates the resistor of pump 1160 to the temperature regulating state to maintain a constant temperature of the fluid below the nucleation energy of the fluid or to maintain a temperature of the fluid constantly within a predefined range of temperatures below the nucleation energy in the fluid according to a predefined or predetermined schedule. In one implementation, the predetermined schedule is a predetermined periodic or time schedule. For example, through historical data collection regarding particular temperature characteristics of fluid testing system 1000, it may have been discovered that the temperature of a particular fluid sample in fluid testing system 1000 undergoes changes in temperature in a predictable manner or pattern, depending upon factors such as the type of fluid being tested, the rate/frequency at which the resistor of pump 1160 is being actuated to the pumping state, the amount of heat emitted by temperature regulator 60 during a pumping cycle in which an individual vapor bubble is created, the thermal properties, thermal conductivity, of various components of fluid testing system 1000, the spacing of the resistor of pump 1160 and sensor 1138, the initial temperature of the fluid sample when initially deposited into sample input port 1018 or into testing system 1000 and the like. Based upon the prior discovered predictable manner or pattern at which the fluid sample undergoes changes in temperature or temperature losses in system 1000, Processor 1510 outputs control signals selectively controlling when the resistor of pump 1160 is either on or off as described above and/or selectively adjusting the characteristic of the resistor of pump 1160 or multiple pumps 1160 when the resistor of pump 1160 is in the "on" state so as to adapt to the discovered pattern of temperature changes or loss and so as to maintain a constant temperature of the fluid below the nucleation energy of the fluid or to maintain a temperature of the fluid constantly within a predefined range of temperatures below the nucleation energy. In such an implementation, the predefined periodic timing schedule at which processor 1510 actuates the resistor of pump 1160 to a temperature regulation state and at which processor 1510 selectively adjusts an operational characteristic of resistor to adjust the heat emitting rate of the resistor of pump 1160 is stored in memory 1512 or is programmed as part of an integrated circuit, such as an application-specific integrated circuit.

In one implementation, the predefined timing schedule at which processor 1510 actuates pump 1160 to the temperature regulating state and at which processor 1510 adjusts the operational state of pump 1160 in the temperature regulating state is based upon or is triggered by insertion of a fluid sample into testing system 1000. In another implementation, the predefined timing schedule is based upon or triggered by an event associated with the pumping of the fluid sample by the resistor of pump 1160. In yet another implementation, the predefined timing schedule is based upon or triggered by the output of signals or data from sensor 1138 or the schedule or frequency at which sensor 1138 is to sense the fluid and output data.

In another user selectable mode of operation, processor 1510 selectively actuates the resistor of pump 1160 to the temperature regulating state and selectively actuates the resistor of pump 1160 to different operational states while in the temperature regulating state based upon signals from temperature sensors 1175 indicating the temperature of the fluid being tested. In one implementation, Processor 1510 switches the resistor of pump 1160 between the pumping state and the temperature regulating state based upon received signals received from temperature sensors 1175 indicating a temperature of the fluid being tested. In one implementation, processor 1510 determines the temperature the fluid being tested based upon such signals. In one implementation, processor 1510 operates in a closed loop manner in which processor 1510 continuously or periodically adjusts the operational characteristic of the resistor of pump 1160 in the temperature regulating state based upon fluid temperature indicating signals being continuously or periodically received from a sensor 1175 or more than one sensor 1175.

In one implementation, processor 1510 correlates or indexes the value of the signals received from temperature sensors 1175 to corresponding operational states of the resistor of pump 1160 and the particular times at which such operational states of the resistor were initiated, the times which such operational state of the resistor were ended and/or the duration of such operational states of the resistor of pump 1160. In such an implementation, processor 1510 stores the indexed fluid temperature indicating signals and their associated resistor operational state information. Using the stored indexed information, processor 1510 determines or identifies a current relationship between different operational states of the resistor pump 1160 and the resulting change in temperature of the fluid within the microphone a channel As a result, processor 1510 identifies how the temperature of the particular fluid sample or a particular type of fluid within the microfluidic channel respond to changes in the operational state of the resistor pump 1160 in the temperature regulation state. In one implementation, processor 1510 presents the displayed information to allow an operator to adjust operation of testing system 1000 to account for aging of the components of testing system 1000 or other factors which may be affecting how fluid response to changes in operational characteristics of the resistor of pump 1160. In another implementation, processor 1510 automatically adjusts how it controls the operation of the resistor of pump 1160 in the temperature regulating state based upon the identified temperature responses to the different operational state of the resistor. For example, in one implementation, processor 1510 adjusts the predetermined schedule at which the resistor of pump 1160 is actuated between the "on" and "off" states or is actuated between different "on" operational states based upon the identified and stored thermal response relationship between the fluid sample and the resistor. In another implementation, processor 1510 adjusts the formula or formula controlling how processor 1510 responds in real time to temperature signals received from temperature sensors 1175.

Although, in the example illustrated, mobile analyzer 1232 is illustrated as comprising a tablet computer, in other implementations, mobile analyzer 1232 comprises a smart phone or laptop or notebook computer. In yet other implementations, mobile analyzer 1232 is replaced with a stationary computing device, such as a desktop computer or all-in-one computer.

Remote analyzer 1300 comprises a computing device remotely located with respect to mobile analyzer 1232. Remote analyzer 1300 is accessible across network 1500. Remote analyzer 1300 provides additional processing power/speed, additional data storage, data resources and, in some circumstances, application or program updates. Remote analyzer 1300 (schematically shown) comprises communication interface 1600, processor 1602 and memory 1604. Communication interface 1600 comprise a transmitter that facilitates communication between remote analyzer 1300 and mobile analyzer 1232 across network 1500. Processor 1602 comprises a processing unit that carries out instructions contained in memory 1604. Memory 1604 comprises a non-transitory-computer-readable medium containing machine readable instruction, code, program logic or logic encodings that direct the operation of processor 1602. Memory 1604 further to store data or results from the fluid testing performed by system 1000.

Figure 22:
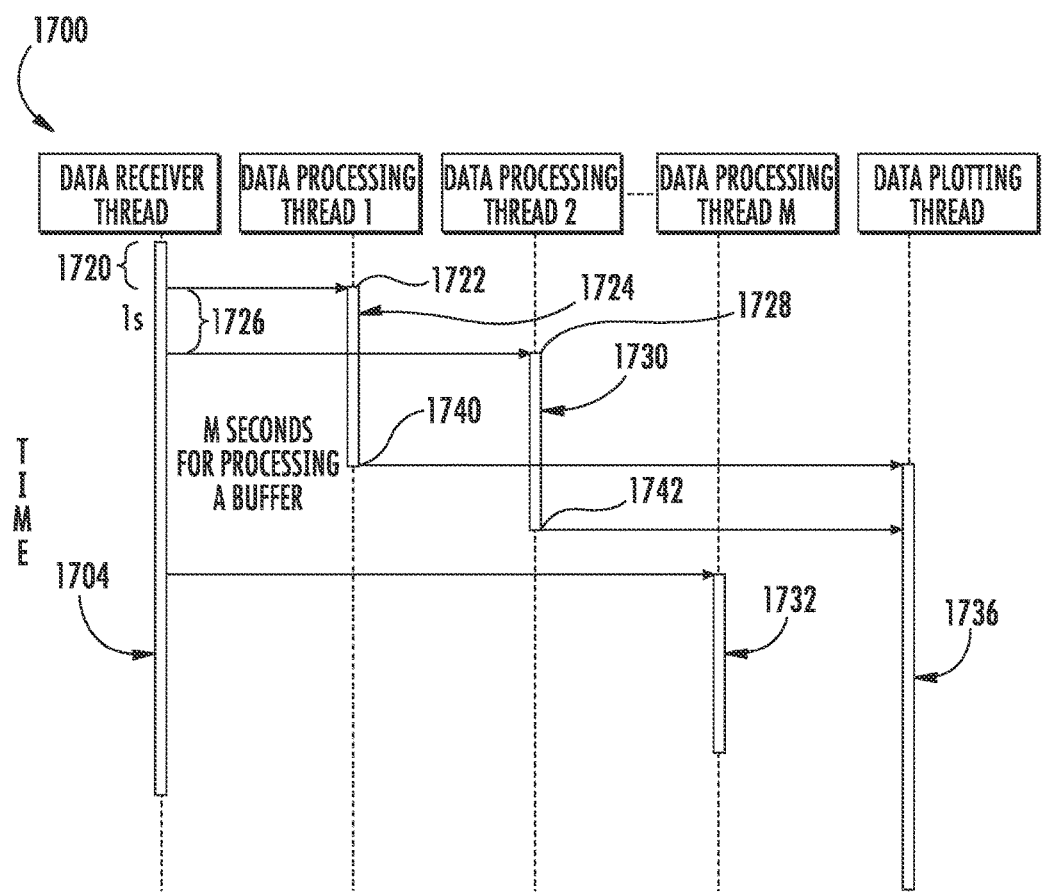
FIG. 22 is a diagram illustrating an example multi-threading method carried out by the fluid testing system of FIG. 7.

As further shown by FIG. 7, memory 1512 additionally comprises buffer module 1530, data processing module 1532 and plotting module 1534. Modules 1530, 1532 and 1534 comprise programs, routines alike which cooperate to direct processor 1510 to carry out and multi-threaded fluid parameter processing method as diagrammed in FIG. 22. FIG. 22 illustrates and describes the reception and processing of a single data receiver thread 1704 by processor 1510. In one implementation, the multi-threaded fluid parameter processing method 1700 is concurrently performed by processor 1510 for each of multiple concurrent data receiver threads in which multiple data sets are concurrently being received. For example, in one implementation, processor 1510 concurrently receives data signals representing sets of data regarding electrical parameters, thermal parameters and optical parameters. For each data set or series of signals for different parameters being received, processor 1510 concurrently carries out method 1700. All of such data sets being concurrently received, buffered, analyzed and then plotted or otherwise presented or displayed on mobile analyzer 1232.

During testing of a fluid sample, such as a blood sample, processor 1510 continuously executes a data receiver thread 1704 in which signals indicating at least one fluid characteristic are received by processor 1510. In one implementation, the signals received by processor 1510 pursuant to the data receiver thread 104 comprise foundational data. For purposes of this disclosure, the term "foundational data", "foundational signals", "foundational fluid parameter data" or "foundational fluid parameter signals" refers to signals from fluid sensor 1138 that have solely undergone modifications to facilitate use of such signals such as amplification, noise filtering or removal, analog-to-digital conversion and, in the case of impedance signals, quadrature amplitude modulation (QAM). QAM utilizes radiofrequency (RF) components to extract the frequency component out so that the actual shift in phase caused by impedance of the device under test (the particular sensor 1138) is identified.

In one implementation, the signals continuously received by processor 1510 during execution of the data receiver thread 1704 comprise electrical impedance signals indicating changes in electrical impedance resulting from the flow of the fluid through art across an electric field region. The signals continuously received by processor 1510 during execution of the data receiver thread 1704 comprise foundational data, meaning that such signals have undergone various modifications to facilitate subsequent use and processing of such signals as described above. In one implementation, data receiver thread 1704, carried out by processor 1510, receives the foundational impedance data or foundational impedance signals at a rate of at least 500 kHz.

During reception of the foundational fluid parameter signals under the data receiver thread 1704, buffer module 1530 directs processor 1510 to repeatedly buffer or temporarily store a predetermined time quantity of foundational signals. In the example illustrated, buffer module 1530 directs processor 1510 to repeatedly buffer or temporarily store in a memory, such as memory 1512 or another memory, all of the foundational fluid parameter signals received during a one second interval or period of time. In other implementations, the predetermined time quantity of foundational signals comprises all the foundational fluid parameter signals received during a shorter or during a longer period of time.

Upon completion of the buffering of each predetermined time quantity of signals, data processing module 1532 directs processor 1510 to initiate and carry out a data processing thread that executes on each of the foundational fluid parameter signals buffered in the associated and just completed time quantity of foundational fluid parameter signals. As diagrammed in the example of FIG. 3, after the foundational fluid parameter signals, such as impedance signals, have been received from cassette interface 1200 for the first predetermined period of time 1720 and buffered, data processing module 1532 directs processor 1510, at time 1722, to initiate a first data processing thread 724 during which each of the foundational fluid parameter signals received during period of time 1720 are processed or analyzed. For purposes of this disclosure, the terms "process" or "analyze" with reference to foundational fluid parameter signals refers to additional manipulation of the foundational fluid parameter signals through the application of formulas and the like, beyond acts such as amplification, noise reduction or removal or modulation, to determine or estimate actual properties of the fluid being tested. For example, processing or analyzing foundational fluid parameter signals comprises using such signals to estimate or determine a number of individual cells in a fluid at a time or during a particular period of time, or to estimate or determine other physical properties of the cells or of the fluid itself, such as the size of cells or the like.

Likewise, after fluid parameter signals from fluid testing device have been received and buffered for the second predetermined period of time 1726, which consecutively follows the first period of time 1720, data processing module 1532 directs processor 1510 at time 1728, to initiate a second data processing thread 1730 during which each of the foundational fluid parameter signals received during the period of time 1726 are processed or analyzed. As indicated in FIG. 22 and the illustrated data processing thread 1732 (data processing thread M), the described cycle of buffering a predetermined time quantity of signals and then, upon the expiration of the time quantity or period of time, initiating an associated data thread to act upon or process the signals received during the period of time is continuously repeated as the data receiver thread 1704 continues to receive fluid parameter data signals from cassette interface 1200.

Upon completion of each data processing thread, the processed signals or data results are passed or transferred to a data plotting thread 1736 as diagrammed in FIG. 22. In the example illustrated, upon completion of processing of the fluid parameter signals received during the period of time 1720 at time 1740, the results or process data from such processing or analysis are transmitted to data plotting thread 1736, wherein the results are incorporated into the ongoing plotting being carried out by data plotting thread 1736 under the direction of plotting module 1534. Likewise, upon completion of the processing of the fluid parameter signals that were received during the period of time 1726 at time 1742, the results or process data from such processing or analysis are transmitted to data plotting thread 1736, wherein the results are incorporated into the ongoing plot being carried out by data plotting thread 1736 under the direction of plotting module 1534.

As shown by FIG. 22, each data processing thread 1724, 1730 consumes a maximum amount of time to process the predetermined time quantity of foundational signals, wherein this maximum amount of time to process predetermined time quantity of signals is greater than the predetermined time quantity itself. As shown by FIG. 22, by multithreading the processing of fluid parameter signals received during fluid testing, mobile analyzer 1232 serves as a mobile analyzer by processing the multiple signals being received in real time, in parallel, facilitating the plotting of the results by plotting module 1534 in real time, avoiding a reducing any lengthy delays. Processor 1510, following the instructions contained in plotting module 1534, displays the results of the data plotting thread on display 1506 while the data receiver thread 1704 is continuing to receive and buffer fluid parameter signals.

Processor 1510 further transmits data produced by data processing threads 1724, 1730, . . . 1732 across network 1500 to remote analyzer 1300. In one implementation, processor 1510 transmits the data, which comprises the results of the processing carried out in the associated data processing thread, to remote analyzer 1300 in a continuous fashion as the results of the data processing thread are generated during the execution of the data processing thread. For example, results generated at time 1740 during execution a data processing thread 1740 are immediately transferred to remote analyzer 1300 rather than waiting until time 1742 at which data processing thread 1730 has ended. In another implementation, 1510 transmits the data as a batch of data after the particular data processing thread has been completed or has ended. For example, in one implementation, processor 1510 transmits the all the results of data processing thread 1724 as a batch to remote analyzer 1300 at time 1740, the same time that such results are transmitted to data plotting thread 1736.

Processor 1602 of remote analyzer 1300, following instructions provided by memory 1604, analyzes the received data. Processor 1602 transmits the results of its analysis, the analyzed data, back to mobile analyzer 1232. Mobile analyzer 1232 displays or otherwise presents the analyzed data received from remote analyzer 1300 on display 1506 or communicates results in other fashions, whether visibly or audibly.

In one implementation, remote analyzer 1300 receives data from mobile analyzer 1232 that has already been analyzed or processed by analyzer 1232, wherein mobile analyzer 1232 has already performed or carried out some forms of manipulation of the foundational fluid parameter signals or foundational fluid parameter data received from cassette 1010. For example, in one implementation, mobile analyzer 1232 performs a first level of analysis or processing on the foundational fluid parameter data are signals. For example, impedance analysis is done on the mobile analyzer which would give the number of cells passing through the sensor. The results of such processing are then transmitted to remote analyzer 1300. Remote analyzer 1300 applies a second level of analysis or processing on the results received from mobile analyzer 1232. The second level of analysis may comprise application of additional formulas, statistical computations or the like to the results received from mobile analyzer 1232. Remote analyzer 1300 carries out additional, more complex and more time-consuming or processing power burdensome processing or analysis of the data that has already undergone some form of processing or analysis at mobile analyzer 1232. Examples of such additional analysis that is carried out at remote analyzer 1300 includes, but is not limited to, coagulation rate calculation and also analytics on data collected from various mobile analyzers to find trends and provide meaningful suggestions. For example, remote analyzer 1232 may aggregate data from several patients over a large geographic area to facilitate epidemiological studies and identify the spread of disease.

Although the present disclosure has been described with reference to example implementations, workers skilled in the art will recognize that changes may be made in form and detail without departing from the spirit and scope of the claimed subject matter. For example, although different example implementations may have been described as including features providing benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements.

What is claimed is:

1. An apparatus comprising:
a microfluidic channel;
an electric sensor within the microfluidic channel to form an electric field within the microfluidic channel and to output signals indicating an impedance of fluid within the electric field within the microfluidic channel;
a frequency source; and
a controller to execute machine readable instructions to output control signals controlling the frequency source to selectively apply different nonzero frequencies of alternating current at different times to the electric sensor, wherein the machine readable instructions cause control signals to be output by the controller to apply a first non-zero frequency of alternating current to the electric sensor and a second non-zero frequency of alternating current to the electric sensor, wherein the first nonzero frequency comprises a frequency selected by the machine readable instructions as executed by the controller for a first fluid test based upon signal-to-noise performance of the first frequency for the first fluid test and wherein the second frequency comprises a frequency selected by the machine readable instructions as executed by the controller for a second fluid test, different than the first fluid tests, based upon signal-to-noise performance of the second frequency for the second fluid test.

2. The apparatus of claim 1, wherein the control signals to be output by the controller apply a first non-zero frequency of alternating current to the electric sensor and a second non-zero frequency of alternating current to the electric sensor, wherein a value of the second non-zero frequency of alternating current to the electric sensor is based upon signals received from the electric sensor during the application of the first non-zero frequency of alternating current.

3. The apparatus of claim 1, wherein the controller is to output control signals to cause the frequency source to scan across a range of frequencies including the first and second nonzero frequencies.

4. The apparatus of claim 3, wherein the controller is to output control signals to cause the frequency source to scan across the range of frequencies a plurality of times.

5. The apparatus of claim 3, wherein the controller is to output control signals to cause the frequency source to continuously scan across the range of frequencies.

6. The apparatus of claim 3, wherein the controller is to output control signals to cause the frequency source to intermittently scan across the range of frequencies.

7. A method comprising:
applying a first nonzero frequency alternating current to an electric sensor to form a first electric field across a microfluidic channel through which fluid flows;
sensing changes in impedance of the first electric field in response to fluid flow through the first electric field;

selecting a second nonzero frequency alternating current, different than the first nonzero frequency alternating current based upon the changes in impedance sensed during application of the first nonzero frequency alternating current to the electric sensor;

applying the second nonzero frequency alternating current, different than the first nonzero frequency alternating current, to form a second electric field across the microfluidic channel through which fluid flows;

sensing changes in impedance of the second electric field in response to fluid flow through the second electric field.

8. The method of claim 7, wherein the first nonzero frequency of alternating current and the second nonzero frequency of alternating current are both within a single selected range of frequencies, the single selected range being based upon signal-to-noise performance of frequencies within the range for a single fluid test.

9. The method of claim 7 further comprising continuously adjusting a frequency of alternating current being applied to the electric sensor so as to scan across a range of frequencies.

10. An apparatus comprising:
a non-transitory computer-readable medium containing instructions to direct a processor to:
prompt a user for a selection of a test from amongst a plurality of available tests;
selecting a plurality of nonzero frequencies of alternating current to be applied to an electric sensor within a microfluidic channel based upon the selection of the test by the user;
output control signals applying the plurality of nonzero frequencies of alternating current to the electric sensor within a microfluidic channel; and
receive signals responsive to the application of the plurality of nonzero frequencies to the electric sensor, the signals indicating a characteristic of a fluid within the microfluidic channel;
wherein a second nonzero frequency of the plurality of nonzero frequencies is selected to be different from a first nonzero frequency of the plurality of nonzero frequencies, and wherein the second nonzero frequency is selected based upon a change in impedance sensed during application of the first nonzero frequency to the electric sensor.

11. The apparatus of claim 10 wherein the instructions are to direct the processor to scan across a range of frequencies when applying the plurality of nonzero frequencies to the electric sensor.

12. The apparatus of claim 11, wherein the instructions are to automatically select a scan profile based upon the selection of the test by the user, from a plurality of available scan profiles and wherein the control signals are to cause the plurality of nonzero frequencies to be applied to the electric sensor according to the selected scan profile.

13. The apparatus of claim 11, wherein the instructions are to apply continuous scan profile when applying the plurality of nonzero frequencies to the electric sensor.

14. The apparatus of claim 5, wherein the control signals cause a frequency source to continuously scan across the range of frequencies according to a ramped profile.

15. The apparatus of claim 5, wherein the control signals cause a frequency source to continuously scan across the range of frequencies according to an arcuate profile.

16. The apparatus of claim 5, wherein the control signals cause a frequency source to continuously scan across the range of frequencies according to a profile having multiple intermediate linear ramping segments.

17. The method of claim 7 further comprising determining at least one of a size of cells or particles in the fluid and a number of cells are particles in the fluid based upon the sensing of changes in impedance of the second electric field.

18. The apparatus of claim 10, wherein the characteristic comprises a characteristic selected from a group of characteristics consisting of: a size of cells or particles of the fluid proximate the electric sensor; and a number of cells or particles of the fluid proximate the electric sensor.

* * * * *